(12) United States Patent
Fitzgerald et al.

(10) Patent No.: US 7,211,073 B2
(45) Date of Patent: *May 1, 2007

(54) METHODS AND DEVICES FOR RETRIEVAL OF A MEDICAL AGENT FROM A PHYSIOLOGICAL EFFERENT FLUID COLLECTION SITE

(75) Inventors: Peter J. Fitzgerald, Portola Valley, CA (US); Brian K. Courtney, Toronto (CA); Ali Hassan, Mountain View, CA (US)

(73) Assignee: Catharos Medical Systems Inc., Los Gatos, CA (US)

( * ) Notice: Subject to any disclaimer, the term of this patent is extended or adjusted under 35 U.S.C. 154(b) by 103 days.

This patent is subject to a terminal disclaimer.

(21) Appl. No.: 10/803,468

(22) Filed: Mar. 17, 2004

(65) Prior Publication Data

US 2004/0254523 A1    Dec. 16, 2004

Related U.S. Application Data

(60) Provisional application No. 60/456,107, filed on Mar. 18, 2003.

(51) Int. Cl.
*A61M 31/00* (2006.01)
(52) U.S. Cl. .......................... 604/500; 600/431; 600/4; 128/898
(58) Field of Classification Search ............ 604/21, 604/35, 27–34, 240–544, 317, 902, 36, 48, 604/93.01, 264, 503–508, 523–532, 540, 604/543; 600/4, 462, 467, 479, 309, 514; 210/646
See application file for complete search history.

(56) References Cited

U.S. PATENT DOCUMENTS

| 3,903,895 | A | * | 9/1975 | Alley et al. ................. 604/178 |
| 4,666,426 | A | * | 5/1987 | Aigner ...................... 604/6.16 |
| 4,753,640 | A | * | 6/1988 | Nichols et al. ............ 604/247 |
| 6,413,233 | B1 | * | 7/2002 | Sites et al. ................. 604/6.13 |
| 6,562,020 | B1 | * | 5/2003 | Constantz et al. .......... 604/523 |
| 2001/0044591 | A1 | * | 11/2001 | Stevens et al. ............ 604/6.11 |
| 2002/0099254 | A1 | * | 7/2002 | Reza ............................. 600/4 |
| 2003/0040736 | A1 | * | 2/2003 | Stevens et al. ............ 604/532 |
| 2004/0011740 | A1 | * | 1/2004 | Bernard et al. ............ 210/646 |
| 2004/0044302 | A1 | | 3/2004 | Bernard et al. |
| 2004/0167385 | A1 | * | 8/2004 | Rioux et al. ................ 600/373 |
| 2005/0085769 | A1 | * | 4/2005 | MacMahon et al. ..... 604/96.01 |

FOREIGN PATENT DOCUMENTS

| WO | WO 02/058777 | 8/2002 |
| WO | WO 02/060511 | 8/2002 |

* cited by examiner

*Primary Examiner*—Nicholas D. Lucchesi
*Assistant Examiner*—Aamer Syed Ahmed
(74) *Attorney, Agent, or Firm*—Bret E. Field; Bozicevic, Field & Francis LLP

(57) ABSTRACT

Methods and devices for selectively removing an agent from a physiological efferent fluid collection site are provided. A feature of the invention is that a non-occlusive aspiration device is employed to selectively remove the target agent from the site only when the target agent is present in the site. Also provided are systems and kits for performing the subject methods. The subject invention finds use in a variety of different applications, including the selective removal of both therapeutic and diagnostic agents from a variety of different physiological sites.

22 Claims, 21 Drawing Sheets

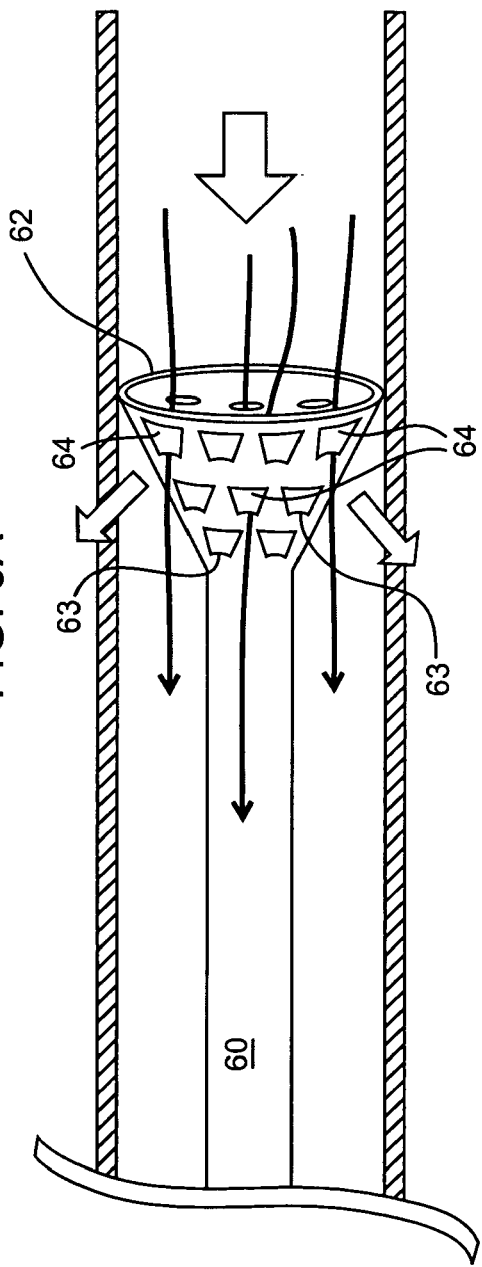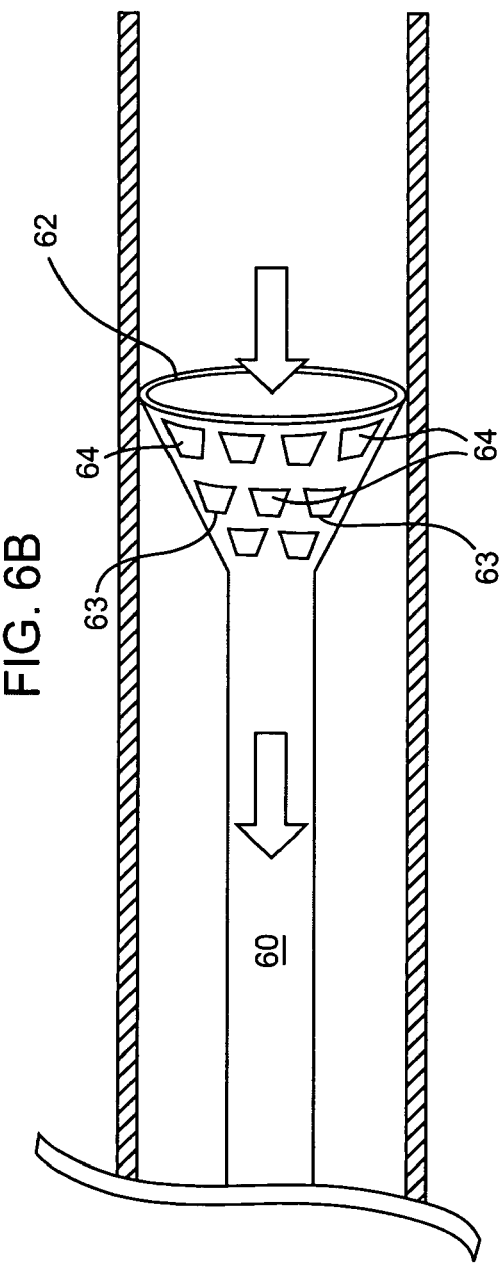

OPEN             CLOSED

OPEN             CLOSED

CLOSED    OPEN

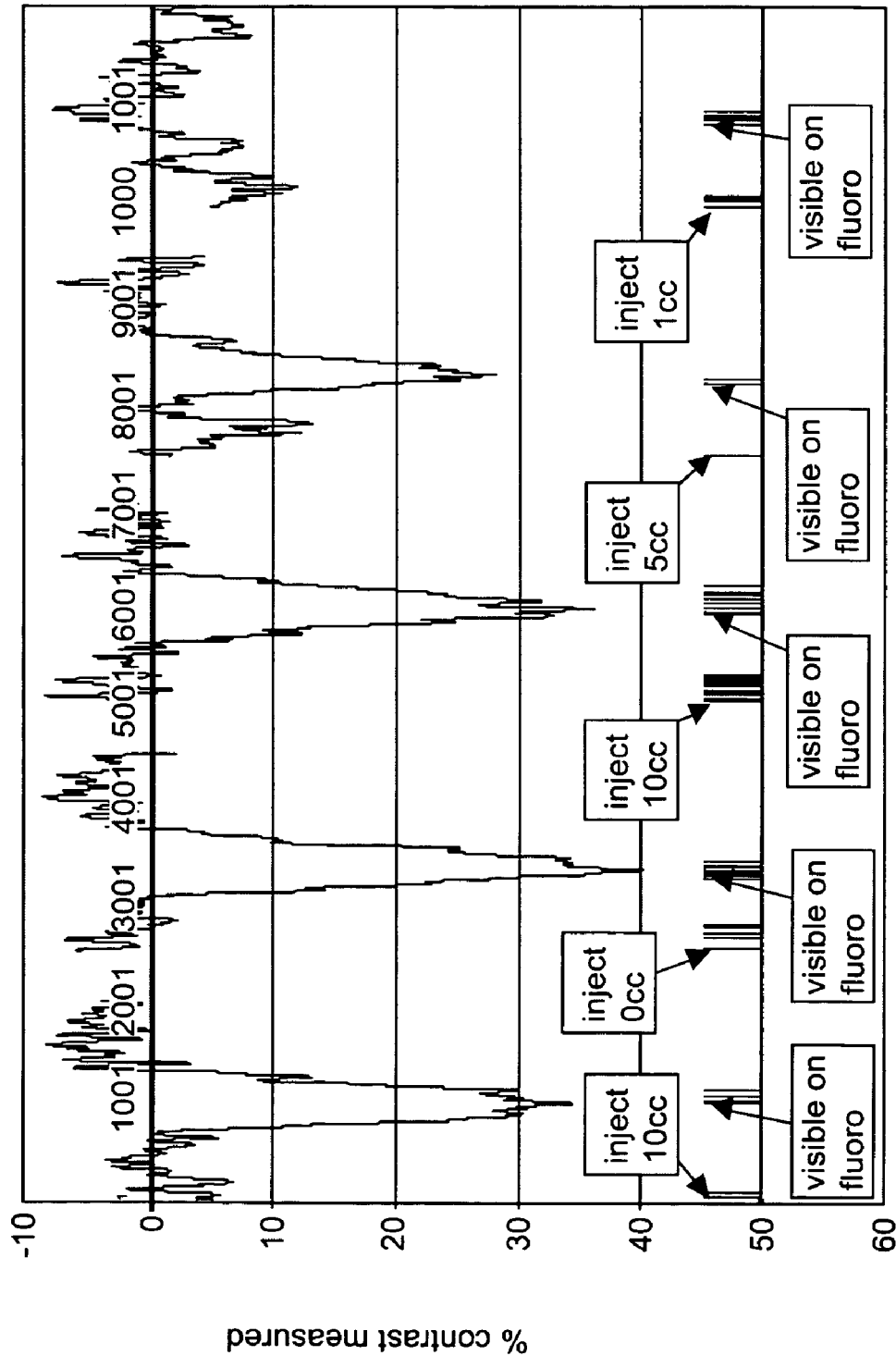

METHODS AND DEVICES FOR RETRIEVAL OF A MEDICAL AGENT FROM A PHYSIOLOGICAL EFFERENT FLUID COLLECTION SITE

CROSS-REFERENCE TO RELATED APPLICATIONS

Pursuant to 35 U.S.C. § 119 (e), this application claims priority to the filing date of the U.S. Provisional Patent Application Ser. No. 60/456,107 filed Mar. 18, 2003; the disclosure of which is herein incorporated by reference.

INTRODUCTION

BACKGROUND OF THE INVENTION

Administration of therapeutic or diagnostic agents to a subject is typically accomplished by either localized or systemic routes. With many types of agents, localized delivery methods are desirable. For example, medical compounds of interest may have desired diagnostic or therapeutic effects within the region into which they are introduced, but also exhibit toxic or other undesirable effects when they are allowed to circulate elsewhere. In certain cases, it is desirable to introduce a higher volume of a compound to the local region than can be tolerated by other body tissues if that volume were to ultimately cause the systemic concentration to exceed a safe threshold.

A common example of such a compound is radio-opaque dye. Iodinated forms of such a dye are used routinely during catheter-based interventional procedures such as coronary, renal, neurological and peripheral arteriography. The iodine component has a high absorption of x-rays and therefore provides a contrast medium for the radiological identification of vessels when introduced within an upstream artery. However, the use of such dyes is known to have potential toxic effects depending on the specific formulation, including direct injury to renal tubule cells, endothelial injury, bronchospasm, inflammatory reactions, pro-coagulation, anti-coagulation, vasodilation and thyrotoxicosis.

Other materials that may be introduced locally for desired effects but whose direct or other effects would be undesired elsewhere include vasoactive agents, cytotoxic agents, genetic vectors, apoptotic agents, anoxic agents (including saline), photodynamic agents, emboli-promoting particles or coils, antibodies, cytokines, immunologically targeted agents and hormones.

An important anatomic concept with respect to the vasculature and other conduits supplying and draining an organ is the principle that a tissue or organ and regions of the organ have a limited number of primary supply conduits and a limited number of draining conduits. Material introduced into the upstream side of the target tissue will typically be dispersed among the diverging arterioles and capillaries, which then reconverge into a collection of common venules and vein(s) downstream, e.g., in a physiological efferent fluid collection site. For example, the myocardium of the heart is fed by the right coronary, left anterior descending and left circumflex arteries. Each of these arteries enters a capillary network that eventually converges into the small and middle cardiac vein, anterior interventricular vein and posterior vein of the left ventricle. These veins are all tributaries of the coronary sinus, which may be viewed as a cardiovascular efferent fluid collection site. Material introduced into any of the aforementioned coronary arteries that travels through the capillary network will enter the coronary sinus providing an opportunity to collect it before it returns to the systemic circulation. In another example, the brain is fed by the carotid and vertebral arteries which enter a highly anastomotic network. Blood flow through the brain substantially drains to the systemic circulation via a network of sinuses that converge onto the internal jugular veins. In yet another example, each kidney is substantially supplied by a renal artery and drained by a renal vein. In yet another example, a tumor or metastatic lymph node may have a set of primary afferent (supply) conduits and a set of primary efferent (drainage) conduits. In yet another example, the lungs are supplied by a pulmonary artery and its branches, and are drained by the pulmonary veins and their tributaries into the left atrium.

As indicated above, there are many instances where localized delivery of an agent is desired. Of particular interest in certain situations is the localized delivery and then subsequent removal of an active agent in an administration approach which would limit the systemic exposure of a subject to an agent even more effectively than localized delivery alone. The present invention satisfies this need.

Relevant Literature

PCT publication Nos. WO 02/058777 and WO 02/060511.

SUMMARY OF THE INVENTION

Methods and devices for selectively removing an agent from a physiological efferent fluid collection site are provided. A feature of the invention is that a non-occlusive aspiration device is employed to selectively remove the target agent from the site, e.g., by removing fluid from the target site primarily when the target agent is at least predicted to be, e.g., anticipated and/or known to be, present in the site. Also provided are systems and kits for performing the subject methods. The subject invention finds use in a variety of different applications, including the selective removal of both therapeutic and diagnostic agents from a variety of different physiological sites.

BRIEF DESCRIPTION OF THE FIGURES

FIGS. 6A and 6B depict another representative catheter aspiration element of a device according to the subject invention, where the aspiration lumen has an expandable distal end, where the distal end may be fenestrated with sealable fenestrae as shown in FIGS. 6A and 6B.

FIGS. 18 to 20 provide graphical results of data obtained during experiments reported in the Experimental Section, below.

DESCRIPTION OF THE SPECIFIC EMBODIMENTS

Figure 1:
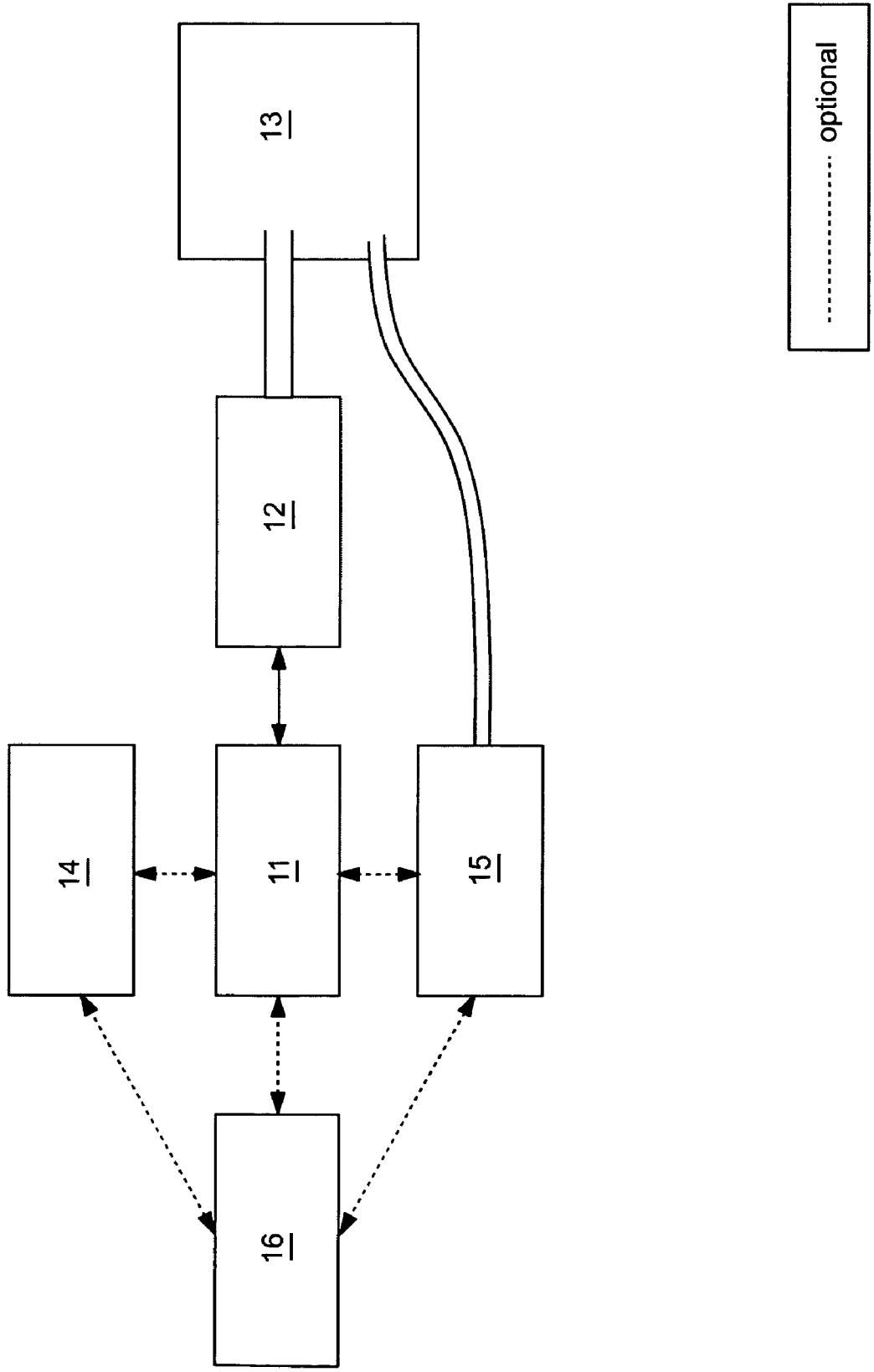
FIG. 1 provides a block diagram of a representative system according to the subject invention.

Methods and devices for selectively removing an agent from a physiological efferent fluid collection site are provided. A feature of the invention is that a non-occlusive aspiration device is employed to selectively remove the target agent from the site, e.g., by removing fluid from the target site primarily when the target agent is at least predicted to be, e.g., anticipated and/or known to be, present in the site. Also provided are systems and kits for performing the subject methods. The subject invention finds use in a variety of different applications, including the selective removal of both therapeutic and diagnostic agents from a variety of different physiological sites.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

As summarized above, the present invention provides methods and devices, as well as systems and kits, for selectively removing an agent from a physiological efferent fluid collection site. In further describing the subject invention, the subject methods are reviewed first in greater detail, followed by a more in-depth description of representative embodiments of systems and devices for practicing the subject methods, as well as a review of various representative applications in which the subject invention finds use. Finally, a review of representative kits according to the subject invention is provided.

Methods

As summarized above, the subject invention provides methods of selectively removing an agent from a host or patient, and specifically from a target site which is a region that is or is proximal to a physiological efferent fluid collection site. By physiological efferent fluid collection site is meant a site in a living entity, that may be naturally occurring or artificially produced (such as by surgical technique), typically an animal, where fluid from two different sources or inputs combines or flows into a single location. Generally the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts, subjects or patients will be humans.

In certain embodiments, the physiological efferent fluid collection site is a vascular efferent fluid collection site, where fluid from at least two different vessels joins into a single vessel. In certain embodiments, the vascular efferent fluid collection site is a cardiovascular fluid collection site, where fluid from at least two different veins joins into a single veinous structure. In a specific embodiment of interest, the cardiovascular efferent fluid collection site is the coronary sinus. In yet other embodiments, as indicated above, the efferent fluid collection site may be an artificially, e.g., surgically produced, fluid collection site, e.g., a non-naturally occurring fluid collection site produced by surgically joining two or more vessels together, etc.

In practicing the subject methods, an agent (which in many embodiments has been locally administered to a subject) is selectively removed from a target site, which target site is the physiological efferent fluid collection site or a region proximal thereto, e.g., downstream therefrom, where when the region is proximal thereto, in certain illustrative embodiments the target fluid removal site is no more than about 40 mm from the efferent fluid collection site, e.g., no more than about 15 mm from the efferent fluid collection site. By selectively removed is meant that the subject methods remove fluid from the target site in a manner that selectively or preferentially removes fluid that is at least predicted to include the agent, where the removed fluid is not returned to the body, at least not without processing to remove the target agent present therein. Depending on the particular protocol and device employed, as described in greater detail below, the fluid may be continuously collected at the fluid collection site but not removed from the body unless it is at least predicted to include agent, e.g., as occurs in those embodiments where fluid is collected at the fluid collection site but immediately shunted back to the subject if it is not at least predicted to include agent. By at least predicted is meant that the bulk or majority of the fluid removed from the site is fluid that is either anticipated to include the agent, e.g., fluid in which the presence of the agent is inferred, or fluid that is known to include the agent, e.g., fluid in which the presence of the agent is detected. Depending upon the particular embodiment of the invention being practiced, in selectively removing fluid from the target fluid collection site and subject, fluid may be removed from the site and subject for a period of time which commences prior to when agent is at least predicted to be in the site, and extend for a period of time after agent is at least predicted to be in the site. In such embodiments, the period of time during which fluid is collected before and/or after agent is at least predicted to be in the site is a fraction or portion of the total period of time during which fluid is removed, typically being less than 50%, such as less than 25% including less than 10–15% of the total time period during which fluid is removed.

In certain embodiments, the subject methods do not remove all fluid from a target and efferent fluid collection site, but just fluid that is at least predicted to include the target agent of interest. In other words, in practicing the subject methods, not all fluid from an efferent fluid collection site present over a given period of time is removed, only fluid that is at least predicted to include the target agent of interest that is to be removed. Put another way, over a given period of time where fluid that does and does not include the target agent flows through the efferent fluid collection site and/or a target fluid collection site, only fluid that is at least predicted, e.g., is anticipated or known to include the agent, is removed from the site and subject, while fluid that does not likely include the target agent is preferentially not removed from the site and subject.

Another feature of certain embodiments of the subject methods is that not all of the agent that is administered prior to practice of the subject methods is removed from the subject. In other words, only a portion of the administered agent is removed from the host or patient by the subject methods. By portion is meant at least about 20%, usually at least about 50% and more usually at least about 70% of the administered agent is removed by the subject methods, where in certain embodiments, the portion removed is at least about 75%, at least about 80%, at least about 90% or more. However, as not all of the agent is collected during practice of the subject methods, in certain embodiments at least 1% of the originally administered agent remains in the subject or patient, such as at least about 5% or at least about 10%.

Agent is selectively removed from the target site, which may or may not be the efferent fluid collection site, according to the subject methods by removing, e.g., aspirating, fluid from the target site and subject/patient/host, substantially only when the target agent is at least predicted to be present in the target site, as described above. As such, when agent is at least predicted to be present in the target site, fluid is removed from the site and host. Conversely, in many embodiments when agent is not predicted to be present in the site, fluid is not removed at least from the host, subject or patient, and in certain embodiments not from the site. Accordingly, in certain embodiments, upon detection or anticipation of agent in the fluid collection site fluid is removed or aspirated from the site and subject, while when the target agent is not detected or anticipated to be present in the site, fluid is not removed from the site, with the exception of a short period of time before and/or after the time when agent is at least predicted to be in the target site, as described above.

In certain embodiments, fluid is selectively removed by actuating a fluid removal element, e.g., aspiration device, such as the devices described below, a defined period of time following administration of the agent to the subject, e.g., an absolute preset period of time, a period of time as defined by a physiological metric, e.g., heart beat, etc.

In certain embodiments, the methods include a step of detecting the presence of target agent in the site and then removing fluid, and agent present therein, from the site in response to detection of the presence of target agent in the site. Typically, when agent is no longer detected in the efferent fluid collection site, the methods stop removing fluid from the site. Thus, fluid is only removed from the efferent fluid collection site and subject over a time period that substantially overlaps the period in which the target agent is present in the efferent fluid collection site.

In practicing these embodiments of the subject methods, the agent may be detected in the fluid collection site using a number of different protocols. In certain embodiments, agent is visually detected by a skilled operator, who then removes fluid in response to visualizing agent, e.g., according to the protocols described below, present in the fluid collection site. In yet other embodiments, agent detection devices that are operatively connected to a fluid removal device are employed, where a signal from the detector that agent is present in the fluid collection site automatically actuates a fluid removal device, e.g., aspiration unit. Representative embodiments of devices that may be employed in such embodiments are described in greater detail below.

To aid in the detection of the agent, in certain embodiments the agent will be one that is labeled with a detectable label, e.g., agent that is has been labeled with a detectable label prior to its introduction into the patient. The agent may be directly labeled with the detectable label, or associated with a detectable label such that the agent is indirectly detectable in that detection of the label also indicates the presence of agent which is presumed or inferred to be within the vicinity of the label. The nature of the label may vary, and may be a radio label, fluorescent label, chromogenic label (e.g., that has a pigment detectable in the optically visible spectrum), etc.

In certain embodiments, the pressure of the target site and/or efferent fluid collection site (which may or may not be the same locations, as described above) and or the tributaries thereof, including a subset of the tributaries thereof, may be modulated, e.g., reduced, in order to achieve the desired collection of agent from the host. The manner in which the pressure may be modulated may vary depending on the particular device employed and manner in which it is implemented, where representative devices and protocols capable of pressure modulation of the target/efferent fluid collection site are described in greater detail below. By modulating the pressure in this manner, one can reduce the pressure within the collection site sufficiently to improve the efficacy of removing the desired agent without causing collapse of the tributaries of the efferent fluid collection site, resulting in a better favorable outcome of the method.

In certain embodiments, devices that include a shunting element, be it a passive or active shunting element, are employed in a manner that modulates the pressure of the target site and/or efferent fluid collection site, as desired. Alternatively and/or in addition thereto, one can use of a pressure sensor within the fluid collection site. The output from such a sensor may be used to optimize the maintenance of the pressure in the collection site so that it is reduced sufficiently in order to increase the likelihood of higher flow to that region from those tributaries that have alternative paths, without causing the collapse of such tributaries.

In certain embodiments, an extension of an aspiration lumen of the device employed is extended selectively into one or more tributaries in order to prevent their collapse during aspiration and to extend the volume from which fluid is aspirated. Alternatively, rather than using a lumen to structurally support the tributaries, a temporary or permanent stent could be introduced to those tributaries prior to aspiration. As a specific example, in certain embodiments the small cardiac vein is stented for such purposes, or a branch of the aspiration lumen from the coronary sinus is extended through the small cardiac vein for such purposes.

In certain embodiments, a specific pattern of aspiration rates that compensates for the delay time between the detection of the desired agent and the activation of the aspiration mechanism is employed. For example, in certain embodiments, there will be a small but finite delay in time between when the agent enters the fluid collection site and when the aspiration mechanism begins to aspirate fluid from the site. During this time delay, some of the fluid containing the agent may have already passed the region from which aspiration normally occurs at the distal portion of the aspiration lumen, thus potentially reducing the efficacy of retrieving the agent. However, by having a higher rate of aspiration for the early portion of the period in which aspiration occurs, as compared to a rate that more closely resembles the normal physiologic rate of flow within the collection site, e.g., where the higher aspiration rate is at least about 2-fold greater, such as at least about 5-fold or 10-fold greater, one can cause that fluid which has already passed the region from aspiration to change direction and return to the aspiration ports. Once this initial period of a higher rate of aspiration has expired, the aspiration rate could then occur at a lower rate which more closely approximates the normal physiologic rate of flow within the collection site, as desired.

In some embodiments, more than one kind of detector is employed to determine the aspiration parameters and time period. For example, in order to ensure that the leading edge of the agent is successfully aspirated, the activation of the aspiration mechanism may be activated by a counter that counts a conservative, pre-selected number of QRS complexes on an EKG after the beginning of injection of the agent, while the trigger to deactivate the aspiration mechanism may be derived from an optical sensor that can recognize when there is no longer any more agent within the fluid being aspirated. Alternatively, inputs from more than one detector can be used in direct combination with each other to determine the aspiration parameters. For example, due to cardiac motion in the region of a fiber optic based sensor, and/or variations in the rate of flow of the fluid in the region of the sensor, the signal produced may vary in a pattern that is reflective of the cardiac cycle, regardless of whether or not the agent to be detected is present, thus producing a noisy signal. In such a case, the fidelity of the sensor may be augmented by using a filtering algorithm that uses the input from an EKG signal to filter the signal produced by the optical detector. By compensating for changes to the output of the optical detector that are due to the cardiac cycle, it may be easier to more accurately characterize the concentration of the agent to be removed in the region of the detector. Any of the detectors mentioned below may be suitably used in combination with each other to further optimize the detection process and/or the efficacy of the aspiration controller.

Practice of the subject methods results in selective removal of an agent from a fluid collection site and subject/patient/host, where the amount of agent removed is, in many embodiments, a substantial portion of (but not all of in certain embodiments) the agent that is present in the subject/patient/host, as described above.

In certain embodiments, the fluid that is removed from the subject or patient may be treated extracorporally, e.g., to remove or neutralize the agent, and then reintroduced into the subject, e.g., where it is desired to minimize the ultimate or final volume of fluid, e.g., blood, that is removed from the subject in a given procedure. For example, where the fluid removed from the subject is blood, the removed blood may be processed with a blood filtering device to remove the agent from the blood, and the processed blood, or at least a component thereof (such as red blood cells) be returned to the patient. Examples of representative fluid, e.g., blood, processing devices include, but are not limited to: the Cell Saver® device (available from Haemonetics); autoLog (available from Medtronic); and the like.

As such, the subject methods may include a step of transferring the harvested fluid into a recirculating system to be reintroduced into the body (as described in U.S. Pat. No. 5,925,016, the disclosure of which is herein incorporated by reference). The recirculating system may incorporate mechanisms to separate the substantially undesirable components from the substantially desirable components. Such a system may incorporate a filter, a centrifugal separator, flow cytometry or other similar apparatuses. The aspiration mechanism may incorporate fluid characterization elements by which aspirated fluid may be characterized, either quantitatively or qualitatively.

Accordingly, in certain embodiments the subject may be one in which it is desired to keep blood loss at a minimum, e.g., the patient may suffer from coronary artery disease, chronic anemia, etc. Extracorporeal processessing and subsequent reinfusion of the treated fluid allows for the reintroduction of the desirable components as an autologous transfusion. Centrifugal mechansims, filter-based systems, dialysis membranes and cell-washing mechanisms are examples of some functional components that can be employed for this purpose.

The methods may be carried out using any convenient system/device, where in certain embodiments, catheter based systems/devices are of interest. Representative systems/devices for use in practicing the subject invention are reviewed in greater detail in the following section.

Representative Devices and Systems

Also provided by the subject invention are devices and systems thereof for selectively removing an agent from an efferent fluid collection site according to the methods described above. The subject devices are devices specifically designed to selectively remove fluid from the efferent fluid collection site, where in certain embodiments of particular interest, as described in greater detail below, the devices are characterized by being non-occlusive, in that they lack an occlusive element, specifically at their distal end. By non-occlusive is meant that, at least while fluid and agent is not being removed from the collection site and subject, fluid enters and leaves the device while not passing outside of the subject, i.e., while remaining intracorporeal. Thus, in certain embodiments, the device is non-occlusive because at no time during its operation does it assume a configuration where the vessel in which it is placed is occluded. In yet other embodiments, the device may be configured so that it collects all fluid at a particular fluid collection site, but then provides for exit of the collected fluid out of the device (when agent is not be removed from the subject) at a location such that the fluid always remains in the body (e.g., at the distal end of the device), and does not pass out of the body prior to its return to the body, i.e., the harvested fluid is always intracorporeal. Depending on the particular device being employed, the fluid may be returned to the body at essentially the fluid collection site, or at a region downstream from the fluid collection site. In these latter embodiments, while the device may be configured to collect all fluid from the fluid collection site, it is non-occlusive for purposes of the present invention because the fluid can be selectively returned to the subject without passing outside of the body, so as to practice the subject methods in which only fluid that is at least suspected of containing the target agent is removed from the subject, as developed more fully above. It should be noted that in these latter embodiments, when fluid at least suspected of containing agent is removed from the body, the device may assume a configuration such that essentially all fluid is collected and removed from the fluid collection site.

The subject systems are collections or combinations of disparate elements that include the subject devices, such as an aspiration element and controller thereof, as well as other components employed in the subject methods, e.g., one or more agent detectors, data recorders/displayers, delivery systems, and the like. See FIG. 1 for a diagram of a system according to the subject invention.

In using the below described representative devices for practicing the subject methods, the aspiration element, e.g., lumen(s), is placed in the at least one region at which fluid from the introduction site(s) of the agent to be removed ultimately converges (i.e., a physiological efferent fluid collection site), such as the coronary sinus. The aspiration mechanism communicates to the proximal end of each aspiration lumen and is able to cause the removal of fluid from the region at the distal end of the aspiration lumen. The aspiration controller, when present, contains mechanisms to control the degree to which the aspiration mechanism is activated over time. Optionally, the invention may incorporate the use of a detector that provides one or more signals to the controller that can then be used to determine the timing and degree to which the aspiration mechanism is activated. Optionally, the invention may incorporate the use of one or more signals from the injection/delivery system as inputs to the controller. The controller may include a timer, or a device able to count EKG cycles to determine the degree of activation of the aspiration mechanism over time. Optionally, the invention may incorporate the use of a recording device and/or interactive display to either log and/or display the activity of the system during a procedure, or to change parameters that govern the operation of the system's components.

The subject devices and systems are now described in greater detail separately.

Devices

In certain embodiments of the subject invention, the devices at least include: an aspiration element; which element is typically made up of: (a) at least one non-occluding aspiration lumen; (b) an aspiration mechanism; where in certain embodiments the aspiration element may further include an aspiration controller. Each of these elements, both constant and optional, are now reviewed in greater detail.

Aspiration Lumens

In the subject devices, one or more aspiration lumens are provided, where the aspiration lumen(s) is constructed or configured in such a manner to be introduced into the target collection site, e.g., efferent fluid collection site or a site proximal thereto, e.g., via a body conduit such as the venous vasculature, so that the distal end can be positioned in the target site for collection of the introduced medium. In many embodiments where the target efferent fluid collection site is a cardiovascular efferent fluid collection site, e.g., as in the case of retrieving compound-laden fluid from the coronary sinus, there may be a catheter with a length appropriate for introduction through either a brachial, jugular or femoral access site to be advanced to the coronary sinus, likely over a guidewire or similar element, for percutaneous delivery. In these embodiments, the aspiration lumen is a catheter device, having dimensions sufficient to be introduced into the efferent fluid collection site via a vascular, e.g., veinous route, where such dimensions are known and readily determined by those of skill in the art.

In certain embodiments, the aspiration lumen has more than one diameter along its length. For example, in order to more easily to enter or approach a collection site, the distal portion of the aspiration catheter is of a first diameter such that the distal portion fits within the geometric constraints of the anatomy of the collection site. In order to reduce the resistance to flow along the entire length of the aspiration lumen, the aspiration lumen has a second, larger diameter for one or more proximal segments of the aspiration lumen. In some cases where a high degree of flow may be required in order to successfully aspirate all the fluid that enters the collection site, such a configuration helps to reduce the total resistance of the lumen, which is proportional to the fourth power of the radius and is thus very sensitive to lumen diameter.

As indicated above, the aspiration lumen is, in certain embodiments, specifically constructed to be non-occluding. As such, the aspiration lumen of these embodiments does not include an occlusive element, e.g., a balloon or other element designed to occlude a vessel or conduit. As such, the subject devices of these particular embodiments are occlusive element free devices.

Aspiration Mechanism

In the subject devices, each aspiration lumen is operatively connected to at least one aspiration mechanism. There may be more than one aspiration lumen connected to each aspiration mechanism. The aspiration mechanism serves the purpose of withdrawing fluid from the target region via the aspiration lumens. The aspiration mechanism may, in certain embodiments, then dispose of the fluid, transfer the fluid into a recirculating system to be reintroduced into the body (as described in U.S. Pat. No. 5,925,016, the disclosure of which is herein incorporated by reference), or simply store the fluid in a reservoir, as desired. The recirculating system may incorporate mechanisms to separate the substantially undesirable components from the substantially desirable components. Such a system may incorporate a filter, a centrifugal separator, flow cytometry or other similar apparatuses. The aspiration mechanism may incorporate fluid characterization elements by which aspirated fluid may be characterized, either quantitatively or qualitatively.

One embodiment of the aspiration mechanism is a suitably-sized syringe in fluid communication with the aspiration lumen. Upon activation by the aspiration controller, the plunger of the syringe is retracted, causing the aspiration of fluid. Any of several mechanisms can be used to provide the motor force necessary to retract the syringe. A rotary motor attached to a threaded bar can be used to cause a pullback motion by coupling the plunger to a component similar to a mechanical nut or other thread-receiving implement that attaches to the threaded bar. A variant of such an embodiment is to attach the thread-receiving implement to the motor and have the threaded component on the plunger. Alternatively, a rotary motor can wind a cable attached to the plunger, or a rack and pinion system may be employed. Alternatively, the motor force can come from a preloaded spring that has sufficient energy stored within it to cause the withdrawal of the plunger. Alternatively, the motor force may come from a compressed gas compartment, or a vacuum compartment.

An alternative embodiment is to have a compartment within which a vacuum exists and the withdrawal of substance occurs by allowing fluid communication between the vacuum compartment and the aspiration lumen. This vacuum element would be similar to the principle used for phlebotomy that is incorporated in the Vacutainer® system.

An alternative embodiment is to use a roller pump, whereby rollers external to the aspiration lumen near the proximal end of the aspiration lumen compress a soft portion of the tubing, and push the contents of the lumen towards the proximal end.

An alternative embodiment is to have an aspiration lumen whereby the proximal end of the aspiration lumen is in fluid communication with the ambient environment or a container whose internal pressure is equal to that of the ambient environment so that the pressure differential between the venous circulation and the ambient environment provides a significant portion of the necessary mechanical impetus to cause aspiration.

Yet another alternative embodiment is to have an aspiration lumen whereby the proximal end of the aspiration lumen is placed at a lower altitude than the distal end of the aspiration lumen, so that the difference in potential energy of fluid at each of these locations causes fluid to flow primarily by gravitational forces out the proximal end.

Depending on performance requirements for the particular application at hand, each of these mechanisms may either have strict binary activation (on or off), or their degree of activation may be controllable. Actuators for controlling the extent of activity may include valves, braking mechanisms, electronic controllers, amplifiers and other common mechanisms.

Aspiration Controller

As indicated above, in certain embodiments the aspiration element further includes an aspiration controller. In certain embodiments, however, an aspiration controller is not present, e.g., in those embodiments where the aspiration mechanism is a syringe that is operated manually by a health care professional.

When present, the aspiration controller is an element that actuates the aspiration element in response to an input signal, e.g., where the input signal may be provided by the operator performing the method or a detector element, as described below. The aspiration controller may actuate the aspiration element in a simple on/off manner, or may actuate the aspiration element in a more complex manner, e.g., to varying degrees over time, such that the aspiration controller may provide a way for controlling the degree to which the aspiration mechanism is activated over time.

The aspiration controller accepts one or more inputs. Such inputs can include manual inputs, e.g., from a health care professional performing the method, or signals from one or more detectors or instruments. As such, in certain embodiments, the subject devices are employed with one or more detector components, where the detector components may or may not be integral to the devices, i.e., may or may not be part of the devices.

In certain embodiments of the subject methods, two goals of the process of selectively retrieving an agent after it has been introduced are considered in the design and/or operation of the current invention. The first goal is to retrieve a high percentage of the introduced material, while the second goal is to remove as little of the native fluid (e.g., blood) as possible. In certain embodiments, these goals may be in conflict with each other. For example, the retrieval of a higher percentage of the introduced material may most easily be obtained by aspirating a higher volume of fluid, while the removal of a lower volume of native fluid (e.g., blood) may most easily be obtained by aspirating a lesser volume of fluid. Therefore, it may be desirable to incorporate into the controller a method to vary the concentration threshold at which the aspiration mechanism is activated. A lower threshold would increase the percentage of agent retrieved, while a higher threshold would minimize the amount of native fluid retrieved.

The threshold of agent concentration for activation of aspiration may be different than the threshold of agent concentration for deactivation of aspiration. Alternatively, the rate of aspiration may be a more continuous function of the agent concentration. For example, higher agent concentrations may indicate to the controller that the rate of aspiration may be increased. Alternatively, the rate of aspiration may be a function of both agent concentration and time.

Several other parameters can be controlled to optimize the goals of retrieval and efficiency, depending on the particular protocol being performed. For example, the injection rate and/or aspiration rates may be adjusted to produce an optimal retrieval.

If the aspiration rate were to be less than the physiologically relevant flow rate through the targeted region, then a certain fraction of the introduced agent would flow past the distal end of the aspiration lumen and not be retrieved. Conversely, if the aspiration rate were to be greater than the physiologically relevant flow rate through the targeted region, an excess amount of native fluid may be aspirated, some of which may arrive to the aspiration lumen by travelling in a retrograde manner. Matching the aspiration rate with the physiological flow rate through the targeted region of retrieval provides, in certain embodiments, a desirable optimum solution. A sensor for detecting a flow rate at the distal end of the aspiration lumen may assist in achieving this optimization.

Similarly, at the injection site, if more agent is introduced than can be immediately accepted at the injection site for antegrade flow, that agent may get diverted to the systemic circulation and can thus not be collected efficiently at the targeted collection region. This situation may be seen to occur under fluoroscopy as angiographic dye is injected near coronary ostia, wherein the excess dye flows back into the aorta and is essentially wasted for diagnostic purposes, while still increasing the system concentration of the agent. However, if less agent than can be immediately accepted for antegrade flow is injected into the injection site, the agent will be diluted with native fluid. This early dilution will worsen the efficiency of retrieval of the agent at the target site, since more native fluid will have to be aspirated in order to retrieve a fixed targeted volume of the agent. A sensor for detecting the flow rate at the site of injection is employed, in certain embodiments, to achieve this optimization.

Furthermore, the controller may incorporate a dynamic component in its control algorithm (i.e., it may be an adaptive controller) whereby the percentage of agent retrieved during a cycle of injection/aspiration is sensed, and the controller adjusts parameters for the cycle, such as, but not limited to, a concentration threshold for aspiration and/or the injection rate and/or aspiration rate and/or the duration of aspiration. These adjustments can be made iteratively over consecutive cycles in an attempt to optimize the parameters of injection and aspiration for subsequent cycles.

Optional Detector Components

A number of different detector components may be employed with the subject devices. Possible detectors or instruments that would be generally external to the body include EKG leads, fluoroscopic images, an automated injection system and/or a manually triggered signal from a technician. The controller could then execute a profile of aspiration over time based on the time from injection or manual triggering. Such a profile may be timed over a number of cardiac cycles or over conventional time. The pattern and/or density of pixels in the fluoroscopic images could also be used to recognize the injection and/or migration of material that produces imaging contrast.

In yet other embodiments, detectors of interest include fiber-optic based sensors, temperature sensors, acoustic sensors, pH detectors, capacitance-based detectors, fluid velocity detectors, conductivity detectors and detectors able to detect changes in ferro-electromagnetism or magnetic susceptibility (see e.g., Blood, 1 Jan. 2003, Vol. 101, No. 1, pp. 15–19).

EKG Inputs

In certain embodiments, signals from EKG electrodes are used to provide a physiologically based timer wherein the controller incorporates a delay between the time of injection of material that is based in part or in entirety according to the number of cardiac cycles that have elapsed rather than using absolute time measured in seconds. The two measures of time are combined, in certain embodiments, to develop an algorithm to trigger the pattern of aspiration relative to the time of injection. For example, the algorithm may cause aspiration to begin based after either a preset number of cycles (e.g. 3.5 cardiac cycles) has elapsed, or an absolute amount of time (e.g. 8 seconds) has elapsed, whichever comes first. The use of cardiac cycles is of interest in many embodiments because it is related to the degree of blood flow in most organs. The heart rate may also be used to determine the peak rate of aspiration and the time-course over which the aspiration is active. A more rapid heart rate may indicate that aspiration could be optimized by having the aspiration occur more rapidly and/or over a shorter period of time.

The EKG leads may be either externally placed on the skin, as in conventional EKG and/or may be delivered intracorporally, as done in many electrophysiology studies. In the case of the intracorporal leads, these leads may be incorporated in a guidewire or catheter, such as those used to deliver the aspiration lumen and/or detector to the target site. By incorporating the EKG leads with a catheter and/or guidewire already used in the system, the system of the current invention becomes more seamless, with a lesser dependence on external components.

Imaging-Based Inputs

Algorithms applied to image sequences, such as fluoroscopic image sequences, may be employed to identify the time of injection of a material that produces contrast in an image sequence. A representative embodiment of such an algorithm is one that detects a substantial change in the histogram of the density of pixels in each frame over time. The rate at which the contrast diffuses is subsequently calculated based on the rate of restoration of the histogram of pixel densities to its approximate baseline distribution (as per prior to injection of material). These two parameters are used to develop inputs into the controller of the aspiration mechanism. Other representative algorithms that may be applied include, but are not limited to: texture-based, histogram-based, derivative-based and motion-estimation algorithms. The employed algorithms may be dependent on the region of the anatomy that is imaged and may also accept EKG and/or respiratory signals as inputs to help the algorithm take into account any effects of motion of the region between image frames over the cardiac and/or respiratory cycles. Such algorithms may be deployed in real-time, or may be performed using post-processing on one of the first injections of the material that produces image contrast to help optimize the aspiration parameters for subsequent iterations of the removal of injected material. The advantage of the latter system is that it would have lower hardware requirements than a real-time system, but it would not produce information to the aspiration controller necessary for the iteration during which the optimized aspiration parameters were produced. The computational capabilities and interface circuitry necessary for the rapid optimization of aspiration parameters may not necessarily be incorporated directly into the aspiration controller itself, but may be incorporated in a software and/or hardware system that is either incorporated in the image acquisition device, or directly connected thereto. In this case, the system that detects the time of injection and/or rate of dispersion of the injected material may be configured to send input signals to the aspiration controller that describe its estimates or calculations of one or more of: the time of beginning of injection, the time of end of injection, the amount injected, time-course over which the injection occurred, the rate of dispersion of the material, the region to which the material flowed, the velocity of the leading edge of the material and other parameters. Alternatively, the input signals may directly tell the aspiration controller the time at which to begin aspiration, end aspiration and/or the degree to which aspiration should occur during that time period at either a uniform or variable rate. In this instance, a substantial part of the aspiration controller may be embedded in the system that does the image processing, and the cost of the aspiration controller, which may be a disposable component, can be minimized. Aside from fluoroscopic-based image sequences, similar algorithms could be applied using ultrasound images, computed tomography, magnetic resonance images and other modalities capable of rapidly sequential images over time (image acquisition rate rapid enough to observe the migration of the injected material), as long as the material injected contained a component that produces image contrast in the particular modality of imaging used.

Fiber-Optic Based Inputs

Certain embodiments of the system use one or more fiber-optic based sensors to detect the presence of the introduced material. Fiber optics are extremely cheap, versatile, disposable, biocompatible and non-conducting, making them an ideal material to use for an intracorporeal sensor. One or more fiber optics are delivered separately to the vicinity of the region from which material is to be aspirated, either via the one or more aspiration lumens, or alongside them. Alternatively, the fiber optics are incorporated into one or more of the aspiration lumens, or are delivered via lumen(s) included in the catheter(s) carrying the aspiration lumen(s). Regardless of the specific construction and mode of delivery of the fiber optic strand(s), a variety of modes of optically assaying the blood or other fluid in the vicinity of the region from which material to be aspirated can be used. Light of the visible or infrared wavelengths can be transmitted down a fiber optic strand and used to illuminate a region near the distal end of the fiber. The interaction of light with the fluid in that region can then be measured in several ways to provide information indicative of the composition of the fluid. Scattered or reflected light can be collected down either the same fiber or via another fiber. The scattered or reflected light may change in intensity or its composition in the electromagnetic spectrum or both and such changes can be detected by detectors at the proximal end of the fiber. An alternative embodiment would be to use one fiber to collect light that is emitted from another fiber and use the changes in the light's properties during transmission through the intervening fluid to assess the fluid composition.

Accordingly, a variety of different optic based detection systems or elements may be employed in the devices and protocols of the subject methods, where the optic based detection systems may evaluate transmitted and/or absorbed light in order to determine or evaluate a property, e.g., presence of target agent, in a fluid. As such, in certain embodiments one may perform a spectral analysis of light transmitted through and/or absorbed by a fluid. Alternatively, one may perform a spectral analysis of reflected/scattered light. In certain embodiments, the spectral analysis may be made at one or more finite number of wavelength ranges, e.g., from about 300 microns to about 5000 microns, from about 700 microns to about 2000 microns, from about 900 microns to about 1900 microns, etc. The detection system may include a single fiber optic embodiment or multi-fiber embodiment, where the system may include a relective component.

Normal blood or other physiological fluid will have a measurable interaction with the emitted light that can either be known prior to the use of the device, or calibrated once the fiber optics are put in place, prior to the introduction of the material to be aspirated, so that a more anatomically specific and/or patient specific assessment of the baseline optical properties of that fluid is performed without the effects of the material to be introduced and aspirated. However, once the material to be introduced enters the region which is assayed by the fiber optic system, the system will recognize a concentration-dependent change in the properties of the collected light. That information will be used as an input to the controller to trigger whether or not the aspiration is activated, and perhaps the extent of aspiration that is to occur. A major advantage of this system over a time-based system is that the ability to detect and use an elevation in the concentration of the material to be aspirated in order to trigger the aspiration provides a highly optimized system that removes only that physiological fluid, such as blood, which contains the highest concentrations of the material(s) to be removed.

In some cases, the material to be introduced may be of such a low concentration, or have optical properties which are difficult to detect with sufficient sensitivity and/or specificity. Therefore, it may be desirable to include with the material to be introduced (first component) for therapeutic or diagnostic purposes one or more second components that would be introduced at the same time as the first material. Examples of such second components would include saline, which is clear in visible wavelengths, or fluorescent compounds (or other labeled compounds, e.g., radiolabeled compounds, chromogenically labeled compounds, etc.) that produce specific wavelengths when photons of shorter wavelengths are presented to them, or pigmented compounds. The second component may be incorporated as a functional component of one or more of the molecules of the first component at a site that does not affect the active sites of the first component. The use of these second compositions is to serve as a tag to help identify that the batch of fluid which was introduced has migrated to the targeted region for aspiration by essentially improving the signal to noise ratio of the detection process. In those cases where it is known that there is a different mobility of the first and second components through the vascular beds or other anatomic structures, it may be necessary to assume a delay between the time at which the second component is detected and when the first component is assumed to have reached the target region, and that delay could be incorporated by the aspiration controller in determining the appropriate time to begin and end aspiration. In yet an alternative embodiments, the tag component and agent component may be present in a compartment or containment element, which compartment or containment element serves to keep the tage and agent components in a defined orientation or spatial relationship to each other. Representative compartment or containment elements in which both the tag and agent components may be placed or packaged include, but are not limited to: microbubbles, liposomes, cells, etc.

Several fiber optic based detectors may be required to properly assay the target region's composition as it is possible that one or more of the sensors may appose an anatomical structure and therefore not be directed towards the fluid within the lumen or cavity of the structure. The sensors may be placed at an offset upstream from the distal end of the aspiration ports in order to provide an earlier indication of when the material to be aspirated will arrive near the aspiration ports so that the system can more optimally time its activities via the aspiration controller. Similar sensors could be placed within the aspiration lumen(s) in order to assist in the quantification of the amount of fluid that was successfully retrieved by the system.

In yet other representative embodiments, temperature sensors, such as thermocouples and thermoresistors, are employed to detect the entrance of fluid with a slightly different temperature into the fluid collection site. In these embodiments, one or more temperature sensors are delivered to the target region of aspiration by the same methods as the fiber optics previously mentioned. The introduced fluid, or a substantial portion of it, has a temperature different from body temperature as it is introduced into the body. This temperature difference can be established by having the fluid at less than body temperature prior to being introduced, or the fluid could be heated slightly (e.g., to <50° C.) within or just prior to entering the injection catheter. As the introduced fluid travels through the capillaries or other small conduits between the site of introduction and the site of aspiration, there will be a substantial equalization of temperature of the fluid with the tissue through which it travels. However, the high precision of available temperature sensors is sufficient to detect the residual difference in temperature that is expected as the introduced fluid enters the target aspiration region after its first pass through the perfused organ.

A disadvantage of this approach is that fluid, such as contrast agent, that is allowed to rest for more than a few seconds within the lumen of the injection catheter within the body would have sufficient time to equilibrate thermally with body temperature. This equilibration means that the initial volume of fluid to be introduced, approximately equal to the volume of the lumen of the catheter, would not be detectable as it enters the target aspiration region by thermal means. One method to overcome this limitation is to replace the column of fluid to be removed within the injection lumen(s) with a column of less harmful fluid, such as saline or blood, such that all the potentially harmful fluid to be introduced, such as contrast agent, would not be within the portion of the injection lumen(s) that is within the body prior to the initiation of injection. An alternative method is to heat fluid within the lumen near the very distal end of the injection lumen as it enters the body to establish a temperature gradient with an opposite polarity. This approach could be accomplished by incorporating an electric heating element in the distal end of the injection catheter.

Acoustic Sensors

In yet other representative embodiments, one or more ultrasonic transducers are used in place of, or in addition to, either or temperature-based or fiber-optic based sensor. Such transducers may or may not have a mechanically rotating or translating motion capability, or have a phased-array functionality to control the direction of an emitted acoustic pulse. The transducers are employed to emit a series of acoustic pulses into the region near the distal region of the aspiration lumens. One or more of the transducers can be used to detect either backscattered or propagated acoustic energy. As blood or other physiological fluids in their pure forms are replaced with fluids that contain some of the material introduced upstream, there is a change in the intensity of the acoustic signals that are backscattered from and/or propagated through the region. Other changes of interest include changes in the slope of the frequency spectrum of the signal or changes in the statistical properties of the signal envelope. These changes are used to provide an indication of the presence of fluid laden with the material that was introduced upstream to trigger the aspiration mechanism via the controller.

Other Sensors

Other sensors of interest include, but are not limited to: those that detect a change in pH of the fluid; a change in the dielectric constant between two electrically insulated leads where the fluid is found between the two electrical leads; a change in the conductivity of the fluid between two uninsulated leads through which a very low current is driven through their circuit which includes the fluid within its path; and changes in the magnetic properties of the fluid found between two coils or via a magnetic resonance imaging system; etc.

Positioning and/or Retaining Mechanisms

In some embodiments, a non-occlusive positioning and/or retaining mechanism is incorporated with either or both of the aspiration lumen and detector at the target region. For the purposes of this invention, a positioning mechanism is generally defined as a mechanism that tends to place elements of either an aspiration lumen or a detector in a more desirable general location than might otherwise occur. For example, it may center the aspiration lumen or detector within the target region. Such a mechanism might reduce the resistance to aspiration by distancing the one or more aspiration holes from the wall of the target region. It may improve the accuracy of detection by positioning a detector in a location that is more completely surrounded by the fluid in which the agent to be detected will likely be found. The detector may otherwise have difficulty in detecting the agent to be removed if the detector were in close proximity to the wall or other structures of the targeted region. Furthermore, an expandable, non-occlusive mechanism, may serve the purpose of helping to retain the distal end of an aspiration lumen and/or detector within the targeted region of aspiration. Such a mechanism would assist in assuring the operator that the aspiration lumen will remain in the target region long enough to achieve the desired performance.

Figure 11:
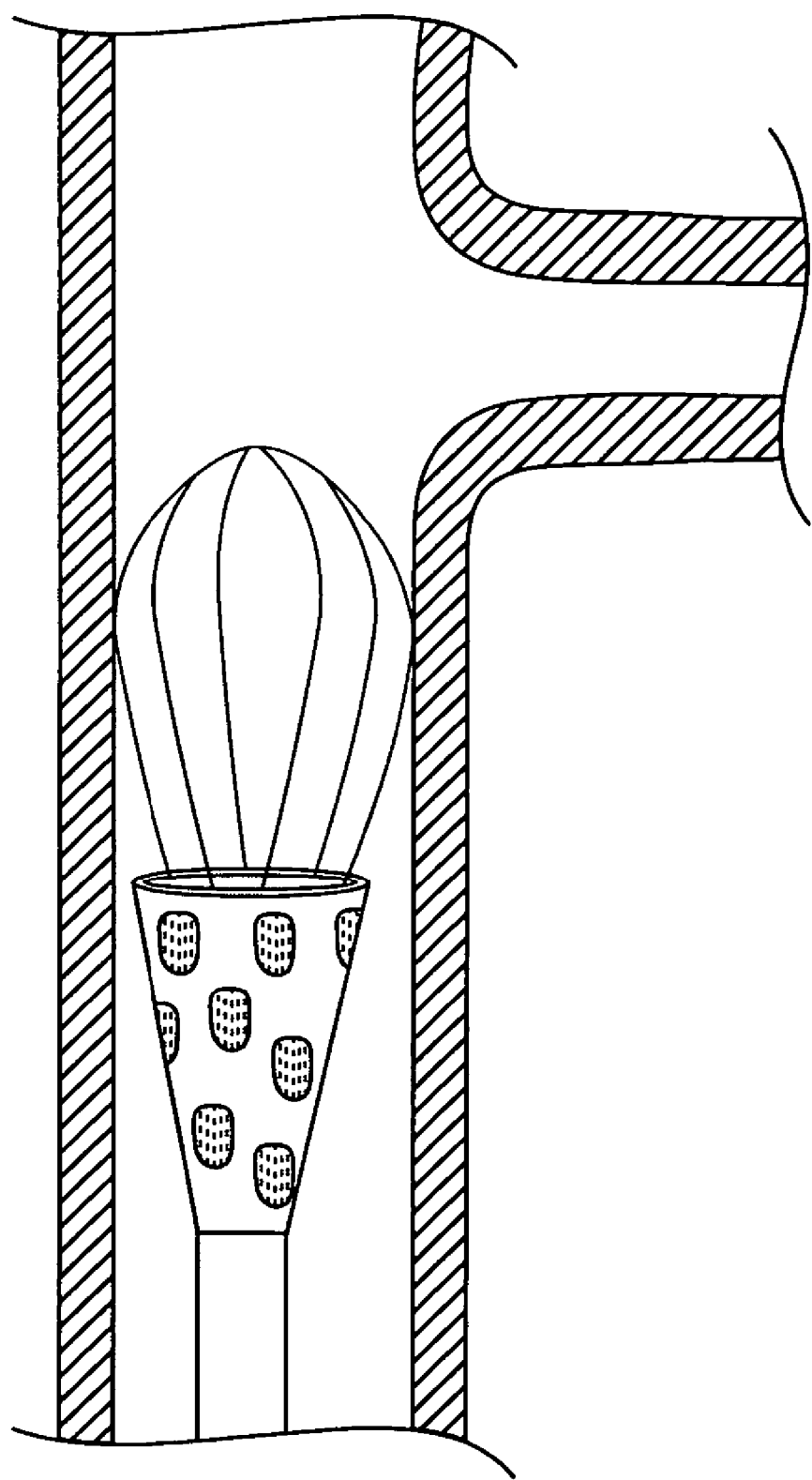
FIGS. 11, 12 and 13 show alternative embodiments of the subject devices that including positioning elements.
Figure 12:
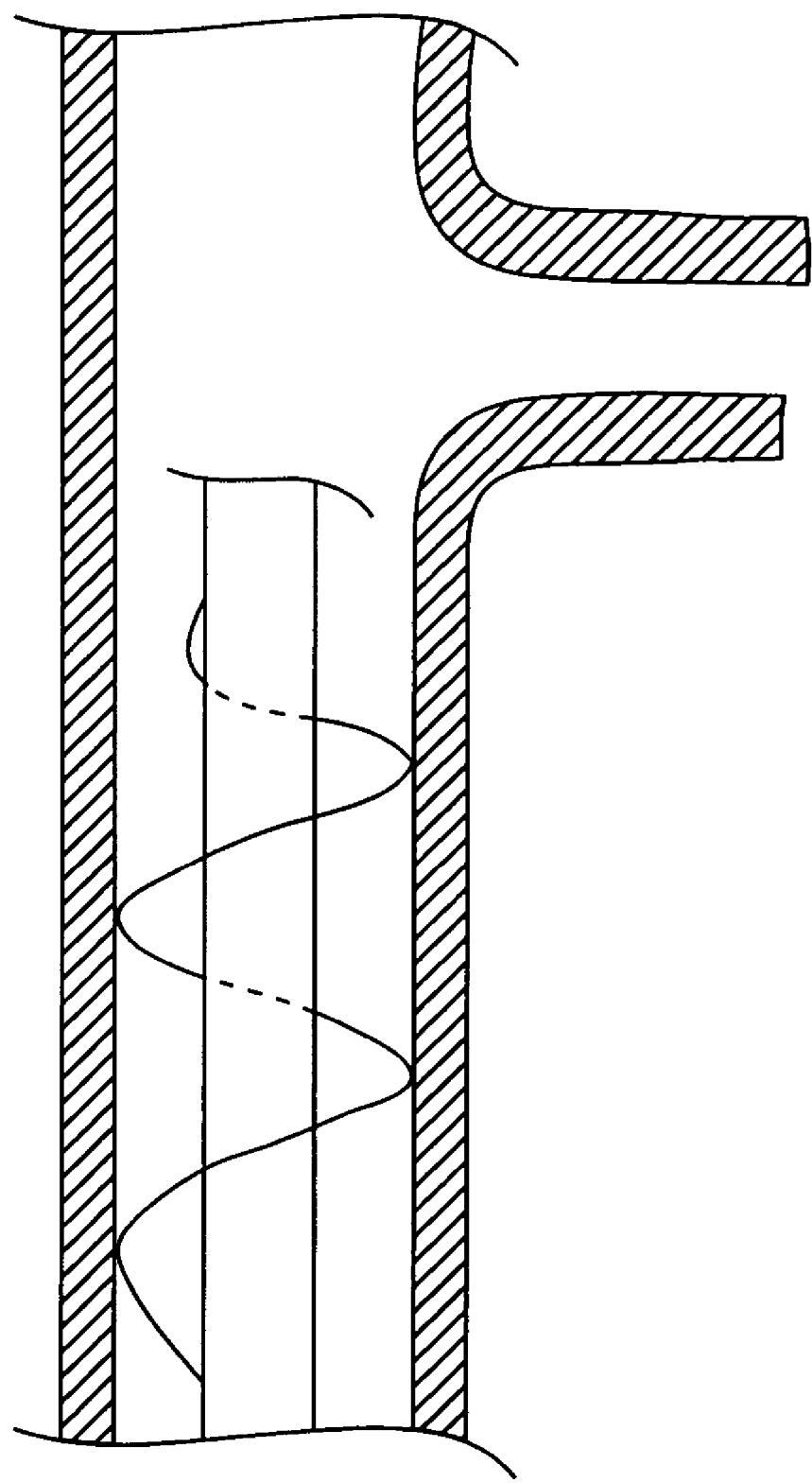
Figure 13:
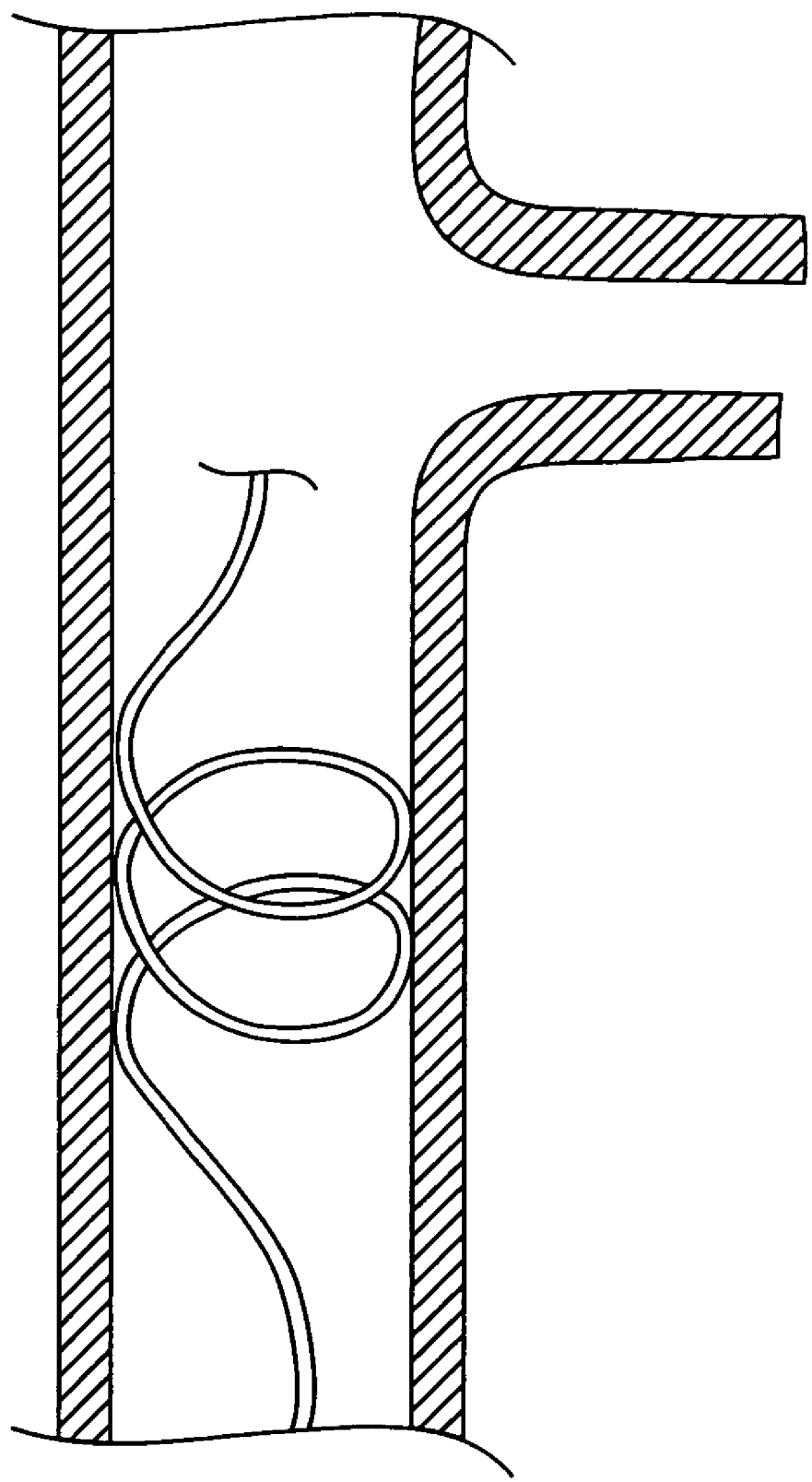

Several embodiments for positioning and/or retaining mechanisms are described, in addition to the non-occlusive funnel-shaped expandable members previously reviewed above. See e.g., FIGS. 11 to 13. One such mechanism includes a set of one or more memory-shaped elements, made of either nitinol, stainless steel, plastic or other similar material. The memory-shaped elements may be in one of at least two states. The first state is in a collapsed form, which enables delivery to the target region. The memory-shaped elements may be held in this configuration by a sheath that surrounds them and retains a collapsed configuration. This sheath may be a separate sheath, or may be the catheter that contains the aspiration lumen, such that the elements are substantially placed within the aspiration lumen while in the collapsed form. Alternatively, the elements may be held in the collapsed form via tension that is applied along a member that travels the length of the catheter onto which they are incorporated, with that member potentially residing substantially within a separate lumen within that catheter. When the detector and/or aspiration lumen are delivered to the target region, the elements may then be allowed to enter an expanded form. Such an expanded form may be similar to the shape of a whisk (as shown in FIG. 11), or in a spiral shape (see e.g., FIG. 12), or several other forms that produce a non-occlusive means of distancing from surrounding structures, such as one or more loops, or a cage. The expansion can be allowed to occur by the operator moving elements at the proximal end of the catheter, or by retracting a sheath or some other similar mechanism. An alternative embodiment is to have the structure of the aspiration catheter and/or detector assume a generally "pig-tailed" shape (see e.g., FIG. 13).

Flow Modulator Element

In certain embodiments, the devices include a flow modulator element for modulating fluid flow through the efferent fluid collection site, at least during removal of fluid therefrom. Accordingly, the device may include an element that changes or alters the nature of fluid flow through the collection site, e.g., by lengthening the fluid flow path, by narrowing the fluid flow path, by changing the velocity of fluid flow through the collection site, etc. For example, the device may include an expandable or deployable element, e.g., balloon, that can be deployed when positioned in the fluid collection site so as to alter a parameter of fluid flow through the site. Depending on the nature of the device and particular protocol being performed, the fluid flow modulation element may be positioned prior to, at substantially the same place as, or after the aspiration element.

Fluid Exit Element

In certain embodiments, the subject devices include one or more fluid exit ports positioned downstream from the distal end of the aspiration element at which enters the aspiration lumen, but still at the distal end of the device. In many embodiments, fluid flow through the fluid exit port or ports is controlled by a flow regulator element which can be moved at least between and "open" and "closed" position, so that flow of fluid out of the aspiration element through the one or more exit ports can be controlled. A variety of different exit portion configurations may be present in these embodiments, including valves, closable windows, etc. Representative embodiments are further described below.

Specific Representative Devices

The devices of the present invention may include one or more of the above described features. The following section describes in further detail various representative embodiments of device that may be employed in practicing the subject methods.

Figure 2:
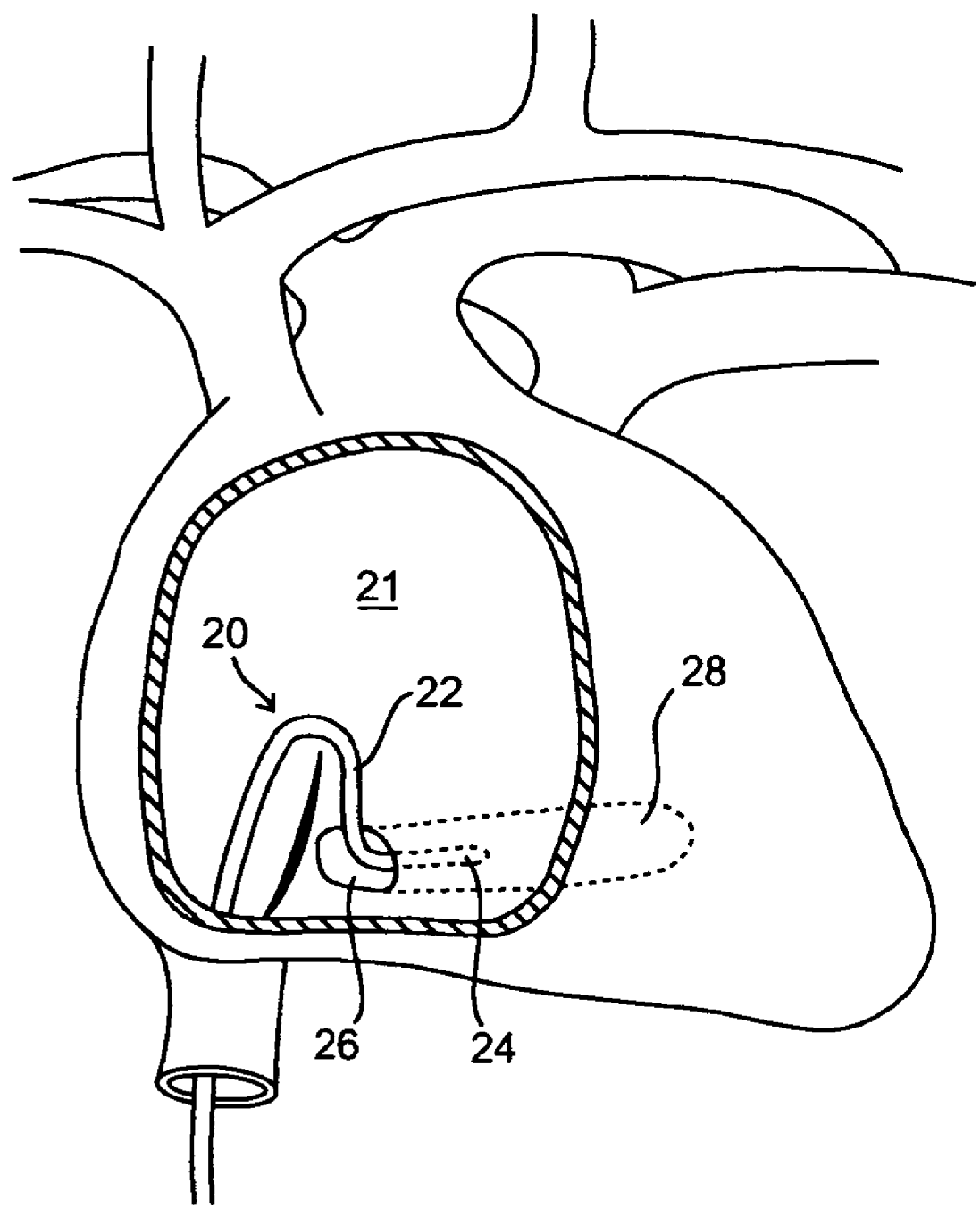
FIG. 2 depicts a non-occlusive catheter whose distal tip obtains a profile that aids in delivering the distal tip into the coronary sinus from the right atrium.

In one embodiment shown in FIG. 2, a representative catheter designed for use in methods of removing agent from the coronary sinus is depicted. In this representative catheter device 20 is an extruded catheter 22 with formation of the tip curvature of the distal end 24 such that it can be more easily delivered to the coronary sinus 28 is provided. The diameter of the catheter in this embodiment is less than the diameter of the entrance 26 to the coronary sinus 28 from the right atrium 21, allowing blood to exit from the coronary sinus when the aspiration mechanism is not activated. Typically, the outer diameter of the distal end 24 of this catheter structure ranges from about 1.0 mm to about 30 mm, such as from about 2 mm to about 7 mm.

Figure 3:
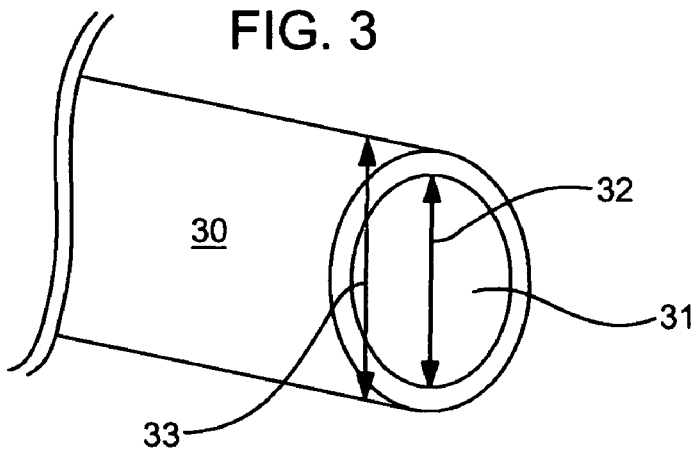
FIG. 3 provides a three dimension view of the distal end of a device according to the present invention.

In certain embodiments, the distal end of the subject catheter is a simple opening, e.g., as depicted in FIG. 3. In the distal end of the device depicted in FIG. 3, aspiration lumen 30 ends at its distal end with opening 31. The inner diameter 32 of the opening ranges from about 1.0 mm to about 30 mm, such as from about 2 mm to about 7 mm. The outer diameter 33 of the distal end may range from about 1.1 mm to about 35 mm, such as from about 2.1 mm to about 7.3 mm.

Figure 4A:
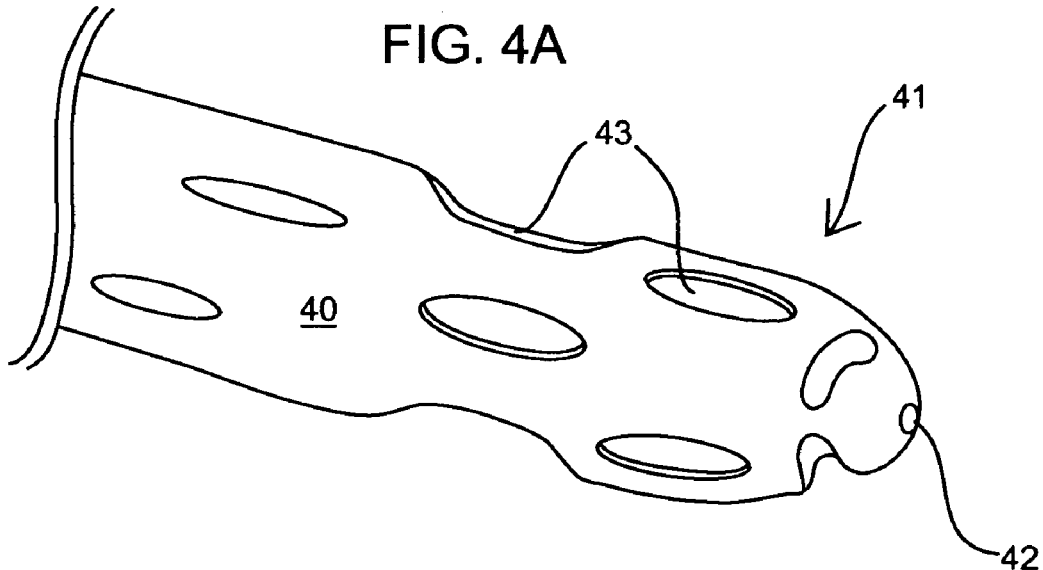
FIGS. 4A and 4B depict representative catheter aspiration elements of devices according to the subject invention, where the distal ends include a plurality of fluid entry ports.
Figure 4B:
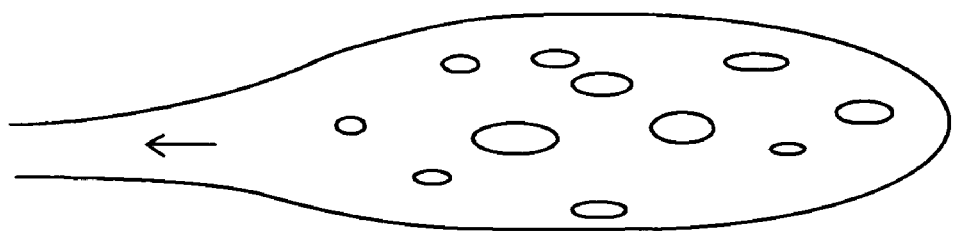

In a variation of the above embodiments, a catheter device with a more rounded tip is provided, as depicted in FIG. 4A. In the representative device shown in FIG. 4A, the distal end 41 of device 40 may have a hole 42 in the distal tip, e.g., for a guidewire to pass through. In addition, there is typically one or more holes 43, e.g., fenestrae, for aspiration, i.e., fluid to enter the aspiration element 40. FIG. 4B provides a depiction of a variation of the device shown in FIG. 4A, where the distal segment of the wall of the catheter may also have one or more holes (i.e., fenestrae) in it, as shown in FIG. 4B. A plurality of holes allows for less trauma to occur during aspiration. If the tip or one side of the distal portion of the aspiration catheter were to be in contact with the wall of the structure to be aspirated (e.g. coronary sinus), holes that are not in contact with the wall would still be able to accept flow from the sinus. This structure minimizes wall injury from aspiration, as well as allows for a more reliable aspiration of fluid. The diameter of the holes or fenestrae 43 may vary widely, but in certain embodiments ranges from about 100 microns to about 7 mm, such as from about 300 microns to about 3 mm. In these embodiments, the distal end of the catheter device/aspiration element is typically not expandable.

Figure 5:
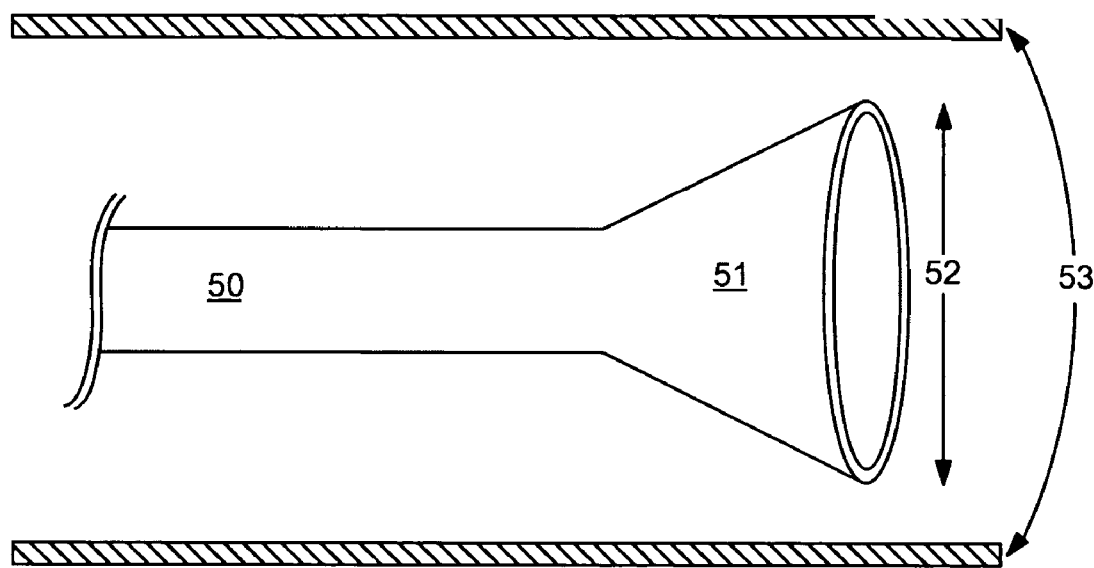
FIG. 5 provides depicts yet another representative embodiment.

In yet another alternative embodiment, such as is shown in FIG. 5, the aspiration catheter tip 51 of device 50 is expandable to a shape that changes flow patterns without occluding flow in the antegrade direction. An example of such an embodiment is an aspiration catheter that is delivered within a delivery sheath (not shown). In using such embodiments, once the distal tip of the aspiration catheter is delivered within the region to be evacuated, the sheath is retracted. The aspiration catheter of these embodiments is constructed such that upon retraction of the sheath, its distal end 51 expands to form the shape of a funnel or similar geometry, where the diameter 52 of the distal end of the funnel may vary, and ranges in representative embodiments from about 2.1 mm to about 50 mm, such as from about 3.0 mm to about 10 mm. This funnel is sized with a maximum diameter such that it is not intended to make circumferential contact with the target region's walls 53. Rather, the funnel is intended to provide a rheological advantage in a non-occluding manner of constraining the general direction from which fluid is retracted during aspiration so as to minimize retrograde flow of blood in the target region upon activation of the aspiration mechanism. By example, in the coronary sinus, it is an intention of this invention to capture fluid flowing in an antegrade direction entering the coronary sinus from the cardiac veins, but not to induce the retrograde entry of blood from the right atrium into the coronary sinus. Of note, because of the non-occluding nature of such a design, blood can flow around the distal tip of the aspiration lumen and proceed along its normal path when the aspiration mechanism is not activated.

Yet another embodiment is a device having a tip that can be expanded to make contact with the walls of the target region for aspiration, but does not result in occlusion of flow due to holes or perforations, e.g., fenestrae, in or near to the distal segment or tip of the catheter. See e.g., FIGS. 6A and 6B. In the device depicted in FIGS. 6A and 6B, device 60 includes distal end 62 which may have a deployable funnel configuration. A plurality of fluid exit ports 63 or fenestrae are provided to provide exit of fluid from the device when aspiration is not occurring. As such, this embodiment helps to create desired flow patterns during aspiration, without occluding flow when the aspiration mechanism is inactive. This embodiment can be constructed by using a mesh-like material for a portion of the funnel-like tip, or by creating holes in a more impermeable material. Optionally, there may be one or more flaps 64 covering the holes or meshwork, such that the fenestrae are sealable. These flaps of this embodiment act as one-way valves, wherein they create minimal resistance to forward flow when the aspiration mechanism is inactive, but provide considerable resistance to retrograde flow when the aspiration mechanism is activated, as they substantially close the holes or pores during aspiration. This closing action occurs primarily as a result of the creation of negative pressure within the region distal to the tip relative to the region outside of the aspiration lumen, proximal to the tip. FIG. 6A shows the device in the absence of aspiration, where blood flows into the distal end of the device and out of the fenestrae or windows, as shown by the arrows. FIG. 6B shows the device during aspiration, where flaps 64 seal the windows 63, causing blood flowing in the distal end of the device to remain in the device and flow in the direction of the arrow to the proximal end of the device and eventually out of the body.

Figure 7A:
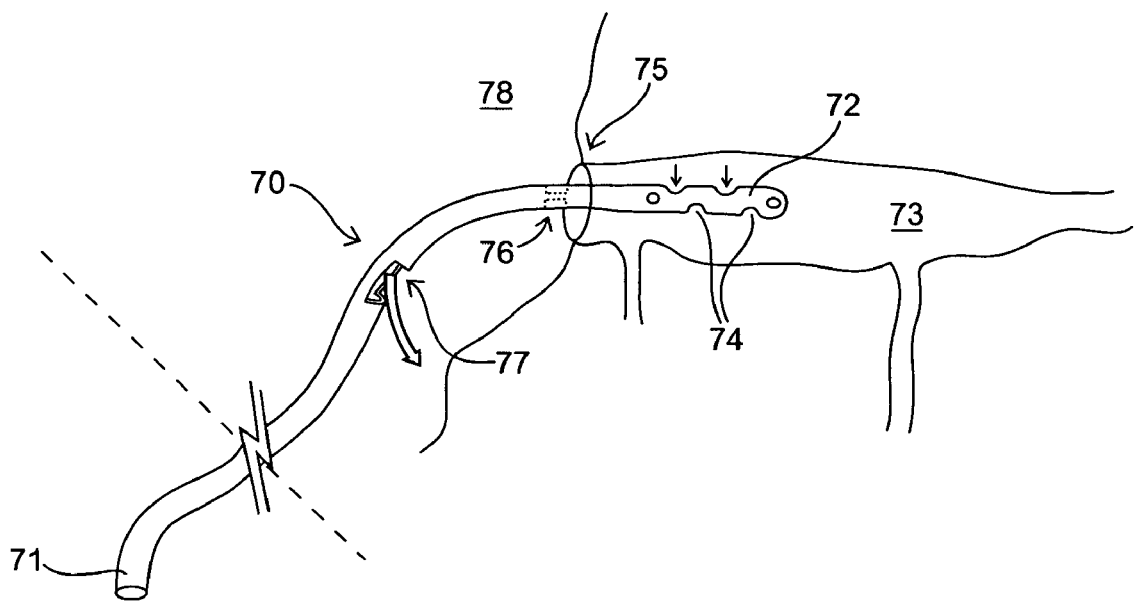
FIGS. 7A and 7B provide a representative embodiment of a device according to the present invention.
Figure 7B:
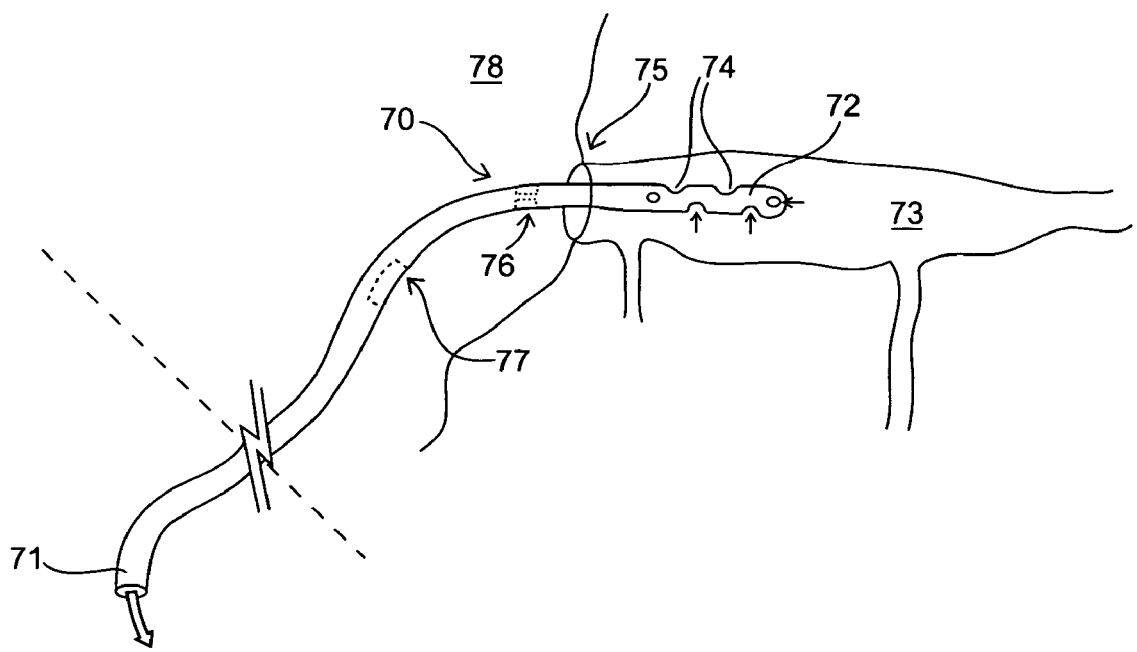

FIGS. 7A and 7B provide yet another embodiment of a device according to the present invention that may be employed to selectively remove target agent from the coronary sinus. In the device depicted in FIGS. 7A and 7B, device 70 includes proximal end 71 and distal end 72. Distal end 72 is shown positioned in the coronary sinus 73. Positioned at the distal end 72 of device 70 are a plurality of fluid inlet ports 74, which allow blood to enter the device upstream of the ostium 75 of the coronary sinus. Positioned on the device on the atrial side of the ostium 75 in right atrium 78 is detector 76, which can detect the presence of agent in fluid passing by the detector. Also present on the atrial side of the ostium 75 is fluid outlet port or window 77, through which fluid can be controllably allowed to flow depending on whether or not the device is in a non-aspirating state, as shown in FIG. 7A, or an aspirating state, as shown in FIG. 7B.

Figure 8A:
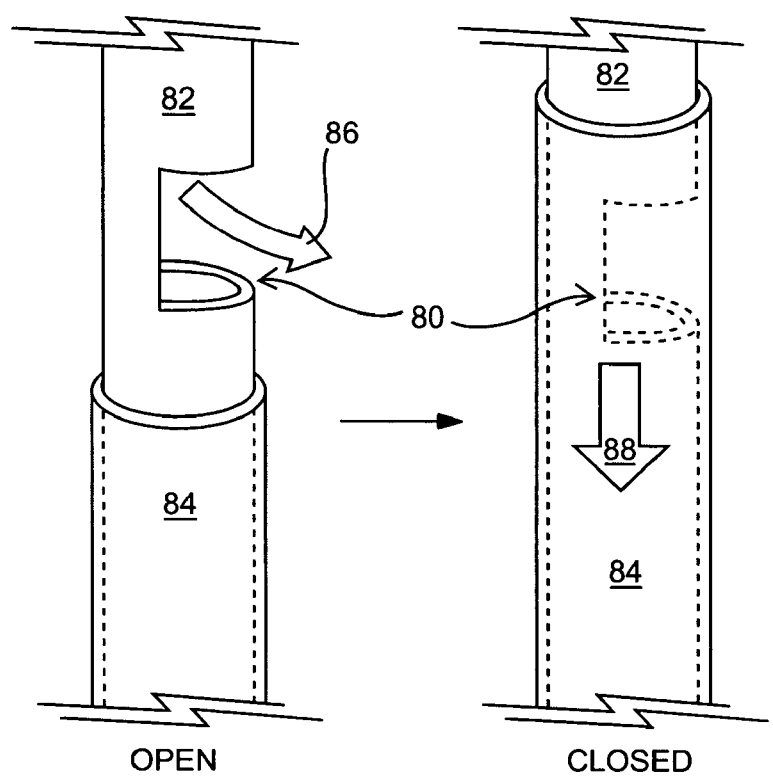
FIGS. 8A to 8C provide depictions of representative embodiments of closable fluid exit ports or windows that may be found on devices according to the present invention.
Figure 8B:
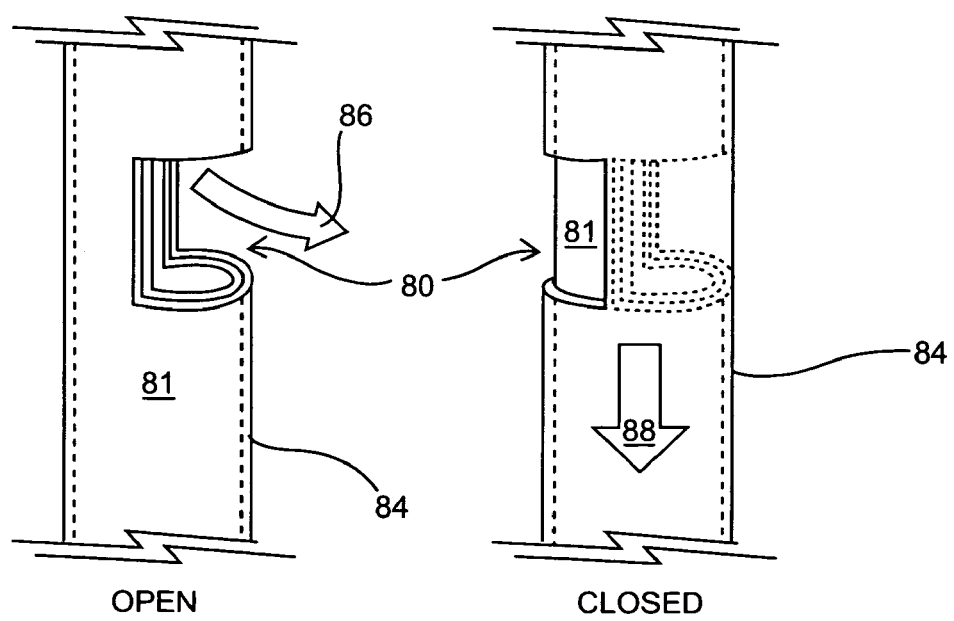
Figure 8C:
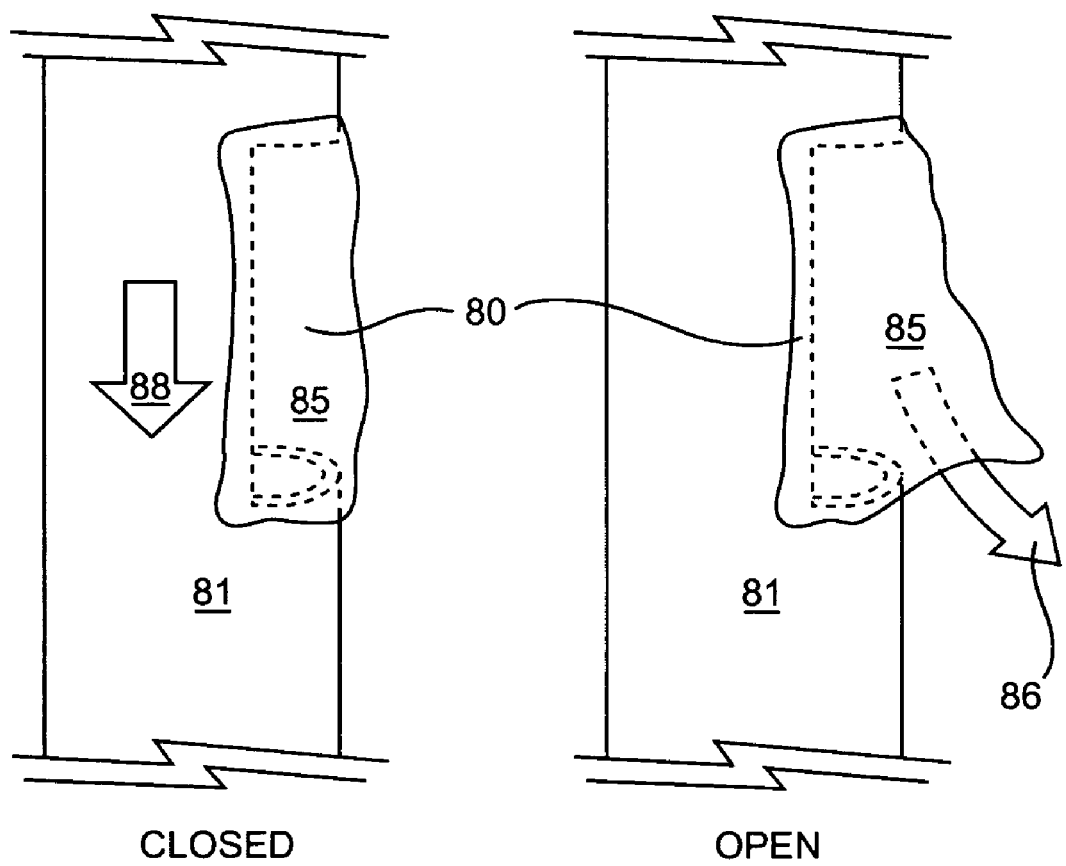

FIGS. 8A to 8C provide depictions of various embodiments of the closable exit port or window 77, of device 70. In FIG. 8A, window 80 is present on a slidable portion 82 which can be moved into and out of sheath element 84 depending on whether it is desired for the window to be open closed. Arrow 86 shows the direction of fluid flow out of the device through window 80 when the window is in the open position. Arrow 88 shows the direction of fluid flow through the device when the window is in the closed position.

In FIG. 8B, window 80 is present on an internal portion 81 whose position relative to sheath element 84 can be rotated depending on whether it is desired for the window to be open or closed, e.g., by rotating internal portion 81 and/or sheath element 84. Arrow 86 shows the direction of fluid flow out of the device through window 80 when the window is in the open position. Arrow 88 shows the direction of fluid flow through the device when the window is in the closed position.

In FIG. 8C, window 80 is present on an internal portion 81 beneath movable flap 85, which flap can be open or closed by provide negative pressure inside of internal portion 81. Arrow 86 shows the direction of fluid flow out of the device through window 80 when the window is in the open position. Arrow 88 shows the direction of fluid flow through the device when the window is in the closed position.

Figure 9:
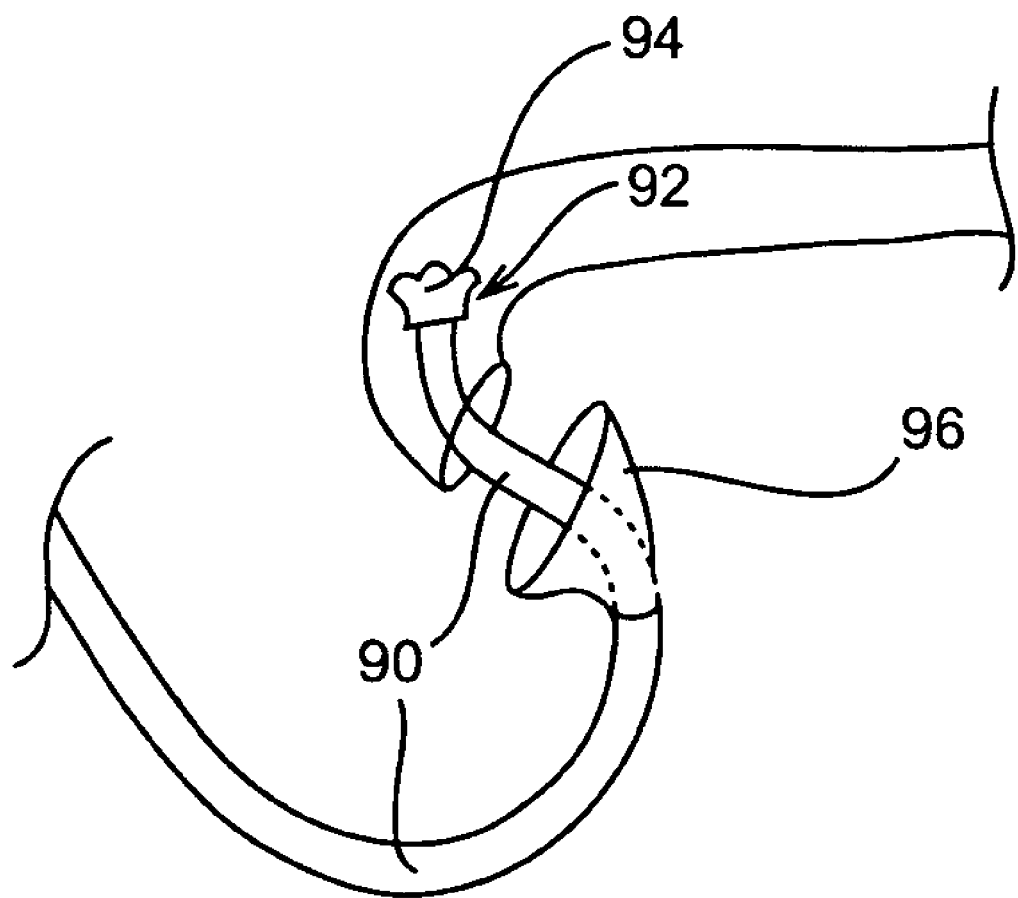
FIG. 9 provides a depiction of a device according to an embodiment of the present invention in which fluid from the coronary sinus is collected into the device in the right atrium.

FIG. 9 provides a depiction of an alternative device for collection of an agent from the coronary sinus using the methods of the subject invention. In the device shown in FIG. 9, device 90 includes distal end 92 having sensing element 94. Proximal to the distal end and positioned inside of the right atrium is collection element or funnel 96. During aspiration, collection element or funnel 96 is deployed as shown in FIG. 9, and collects substantially all fluid flowing out of the coronary sinus through the ostium.

Figure 14A:
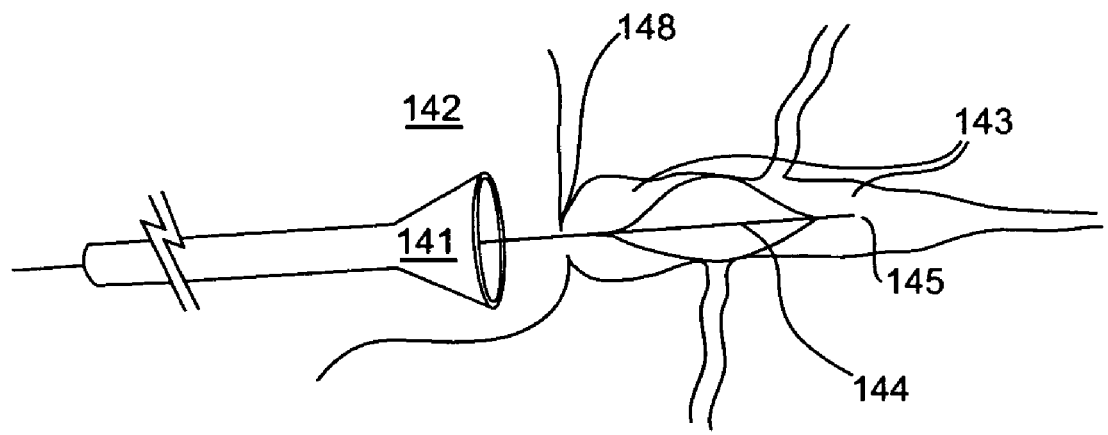
FIGS. 14A to 14C provide different depictions of a device that collects fluid from a target site proximal to an efferent fluid collection site.
Figure 14B:
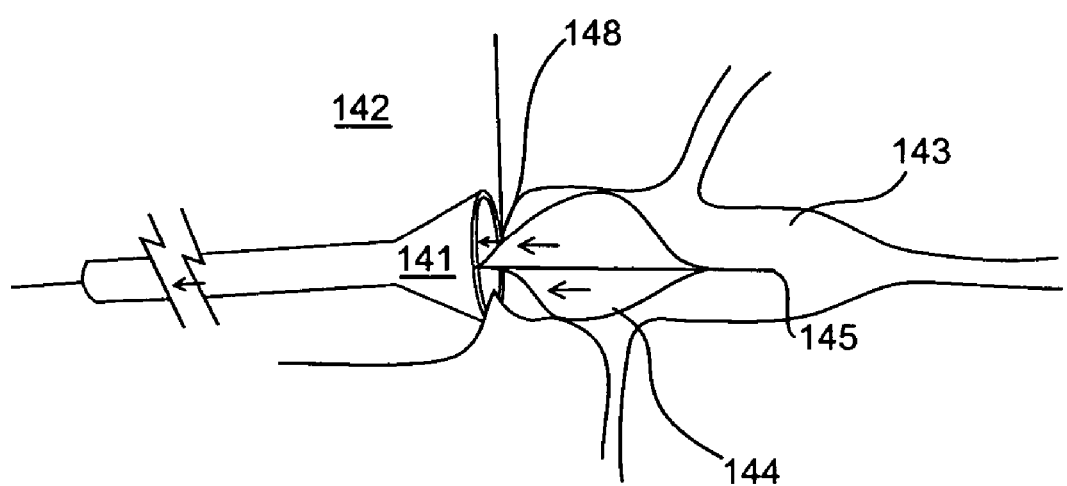
Figure 14C:
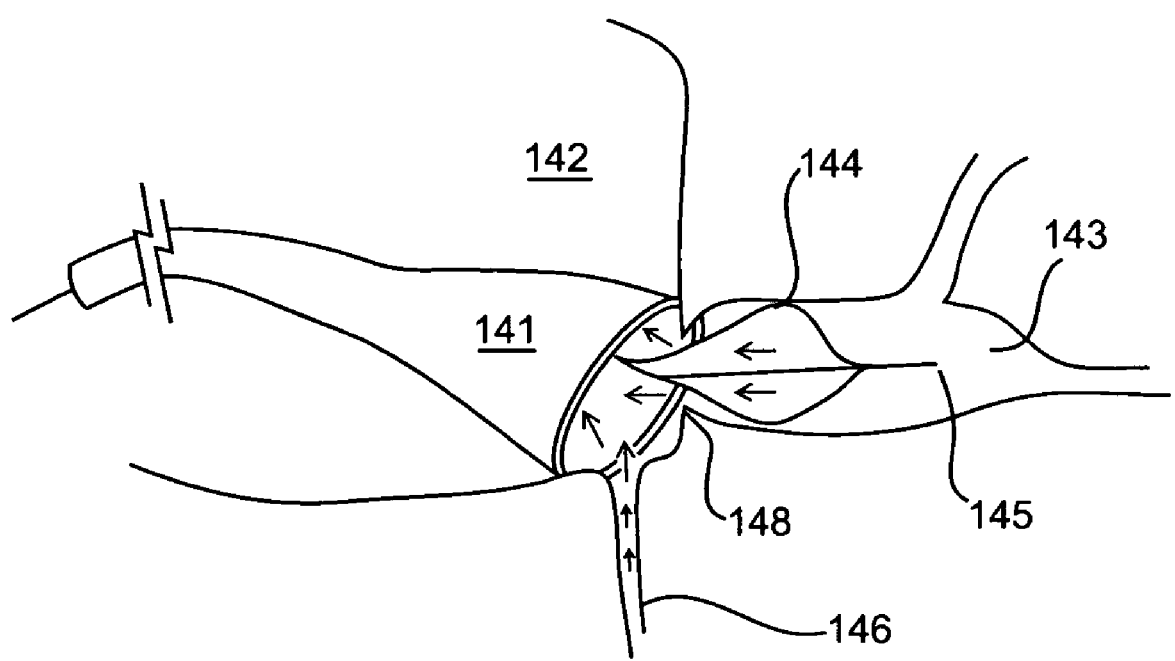

FIGS. 14A to 14C provide depictions of alternative embodiments of the device shown in FIG. 9 in which fluid collection occurs at a target site (i.e., right atrium) proximal to the efferent fluid collection site (i.e., coronary sinus), and illustrates further that the distal portion of the aspiration lumen 141 need not necessarily reside within the site of convergence, such as the coronary sinus, but rather, may reside primarily within a region proximate to the site of convergence, such as the right atrium 142. In using the devices shown in FIGS. 14A to C, as the agent to be removed is sensed within the site of convergence, the aspiration mechanism is activated and the agent to be removed is aspirated as it exits the site of convergence. In certain embodiments, the aspiration lumen is one that can be advanced such that the distal tip of the aspiration lumen enters into closer proximity to the site of convergence. This motion may occur secondary to the act of initiating the aspiration mechanism which would tend to pull the catheter tip forwards, or as the result of a forced translation of the aspiration lumen. Optionally, a guidewire or other shaft 144 may reside within the site of convergence and may contain a sensing element 145. This shaft may have an anchoring element 144 at its distal such that it can be temporarily anchored within the convergence site. An example of such a means would be an expandable member that does not occlude flow, such as a whisk-shaped nitinol element 144. This shaft would be arranged with the aspiration lumen in such a way that the advancement of the aspiration lumen is more effectively directed towards the site of convergence. For example, the shaft could lie coaxially within the aspiration lumen, or within a separate lumen that runs coaxially within the aspiration lumen as part of the aspiration catheter. In the case where the distal end of the aspiration lumen has an element, such as a funnel or similarly shaped tip facing towards the convergence site, whose dimensions are large enough to prevent it from fully entering the convergence site, the aspiration catheter can be translated towards the site of convergence such that the tip forms a temporary seal around an opening into the site of convergence, such as the os of the coronary sinus. See particularly FIGS. 14A and 14B. An advantage of a system such as that shown in FIGS. 14A to 14C wherein the distal tip of the aspiration catheter is expandable to cover an area larger than the primary site of convergence is that if there is an additional conduit 146 in a particular patient or subject through which the agent to be retrieved could escape into the general circulation, such as an anomalous middle cardiac vein that emptied into the right atrium rather than the coronary sinus, the os of both the coronary sinus and the middle cardiac vein can be generally enclosable by the distal tip of the aspiration lumen, thus improving the efficiency of collecting the agent. A further advantage of such an embodiment is that if some of the conduits that converge into the fluid collection site do so at a location very close to the os or exit point of that site, by positioning the distal tip of the aspiration lumen immediately outside of the site (as illustrated in FIG. 14C), the amount of agent that leaks from those conduits that are closest to the os or exit point of the site is minimized. For example, the more conventional anatomy of the middle cardiac vein is for it to drain into the coronary sinus at a point very close to the coronary os. Rather than have the distal portion of the aspiration lumen within the coronary sinus, it may be more advantageous in certain embodiments to use the embodiments described above to have the distal tip of the aspiration lumen in the right atrium near the coronary os. Once the aspiration mechanism is activated, the distal tip of the aspiration lumen can be made to tend to abut against the wall of the right atrium, enclosing the coronary os and any nearby anomalous points of cardiac venous return (see e.g., FIG. 14C).

In a variation of the representative device and its use as depicted in FIGS. 14A to 14C, FIGS. 15A and 15B provide a depiction of a device as shown in FIGS. 14a to 14C where the device further includes a shunting element. In the embodiment of the device shown in FIGS. 15A and 15B, the aspiration lumen is one that produces a seal with the structures that define the collection site such that fluid within the collection site is generally directed to enter into the aspiration lumen and travel within a distal portion of the aspiration lumen. In such an embodiment, the aspiration lumen has one or more exit ports 150 that open into the circulation and would generally allow the fluid that entered the aspiration lumen at the distal end to enter back into the circulation at a more proximal point along the lumen (as described above, e.g., in connection with FIGS. 8A to 8C. When the aspiration mechanism is activated, the one or ports become substantially if not completely closed, thus directing the fluid that enters the distal tip of the aspiration lumen to the extracorporeal components of the present invention, rather than allowing it to directly reenter the circulation from the aspiration lumen. Mechanisms to substantially or completely close the re-entry ports include one or more flaps on the external surface of the lumen that act as one way valves which allow flow to exit the lumen from these ports when the aspiration mechanism is not activated, and prevent flow to enter the lumen from these ports when the aspiration mechanism is activated. Alternatively, an outer shaft can be placed coaxially around the around lumen, and have fenestrations in it that, when aligned with the one or more ports of the aspiration lumen, create a window that allows fluid to escape the aspiration lumen. By a combination of translating and/or rotating the outer fenestrated shaft such that the fenestrations do not align, flow will not able to enter or exit through the re-entry ports. See FIGS. 15A and 15B. In using the devices shown in FIGS. 15A and 15B, the distal tip 141 of such a system may reside within the collection site 142 and have an expandable element to make a seal with the inner surface of the collection site, thus directing fluid through the distal portion of the aspiration lumen. Alternatively, the distal tip can be made to abut against the tissue external to the os 148 or exit point of the collection site, such as the portion of the wall of the right atrium near the coronary os. An advantage of this shunting configuration includes an opportunity to incorporate a sensor within the aspiration lumen in a highly reliable configuration that may improve sensor accuracy as compared to the situation when a sensor may be placed in an anatomical structure. Yet another advantage is that the portion of the aspiration lumen through which fluid travels prior to exiting through the distal exit ports acts as a time-delay circuit, which reduces the performance requirements of the system by allowing the aspiration mechanism to take longer to actuate without concern that some of the agent may have already escaped in the small but finite time period between the time when the agent was detected and when the aspiration mechanism was activated.

Figure 15A:
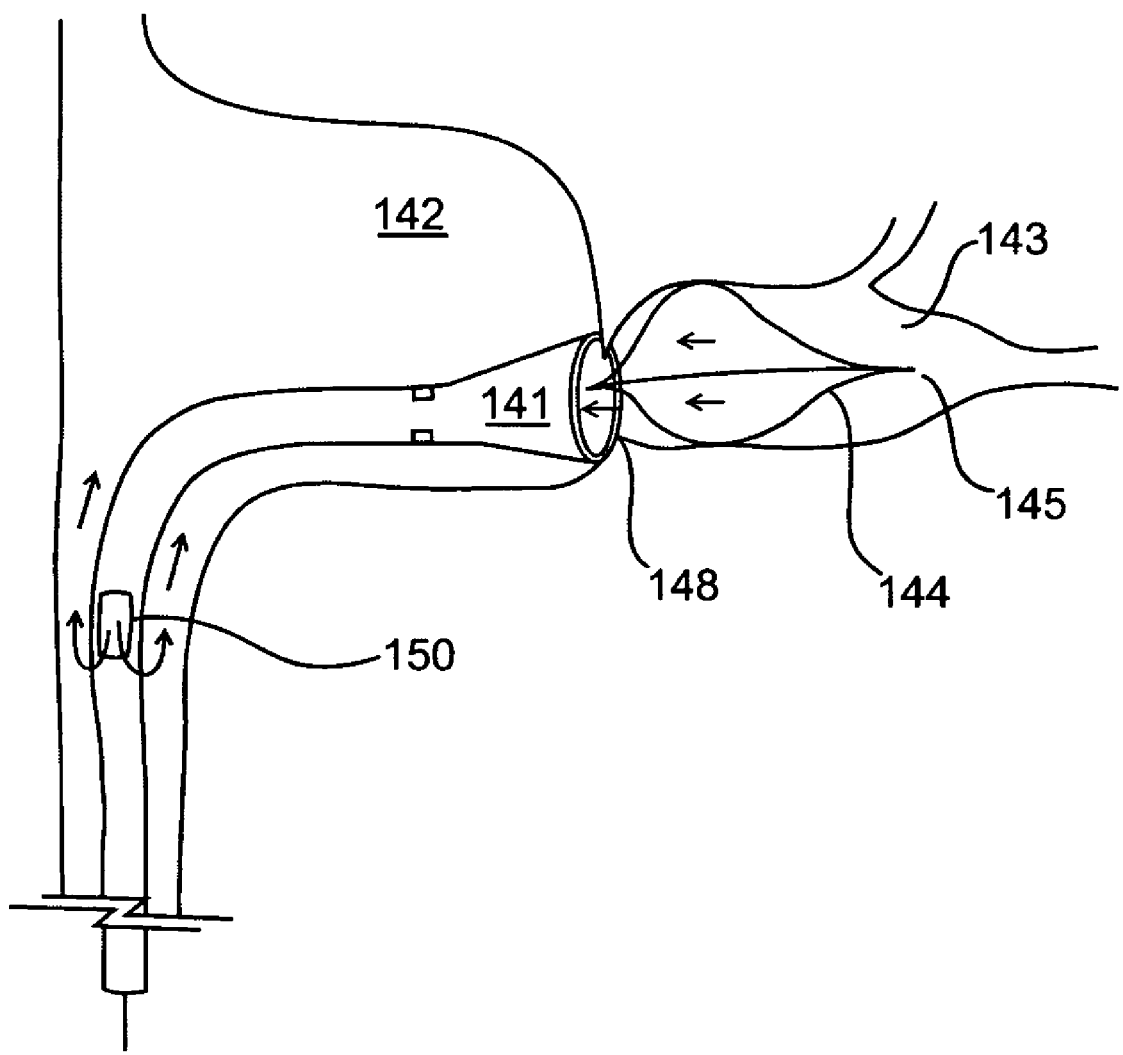
FIGS. 15A to 15B provide different depictions of a device that includes a passive shunting element.
Figure 15B:
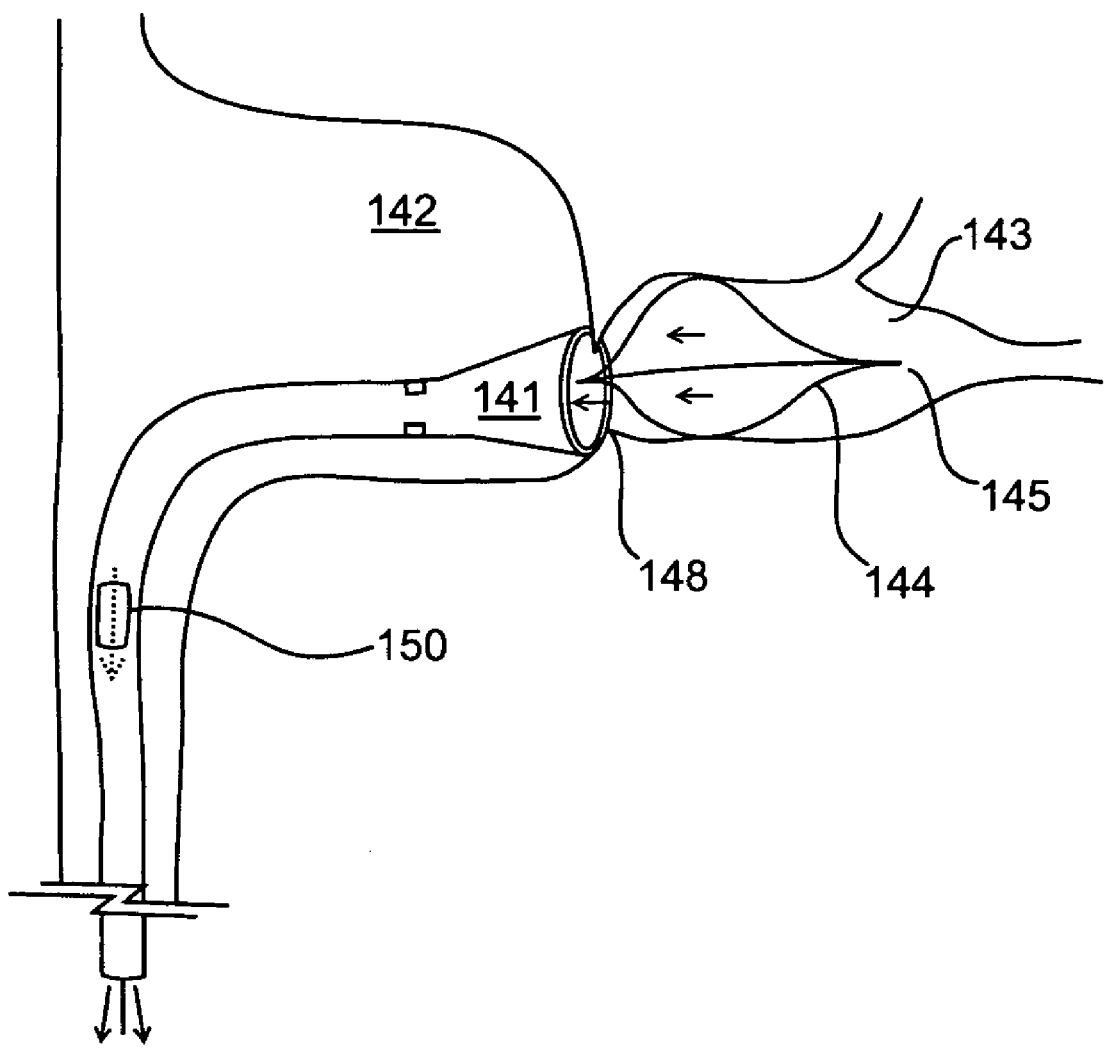
Figure 16A:
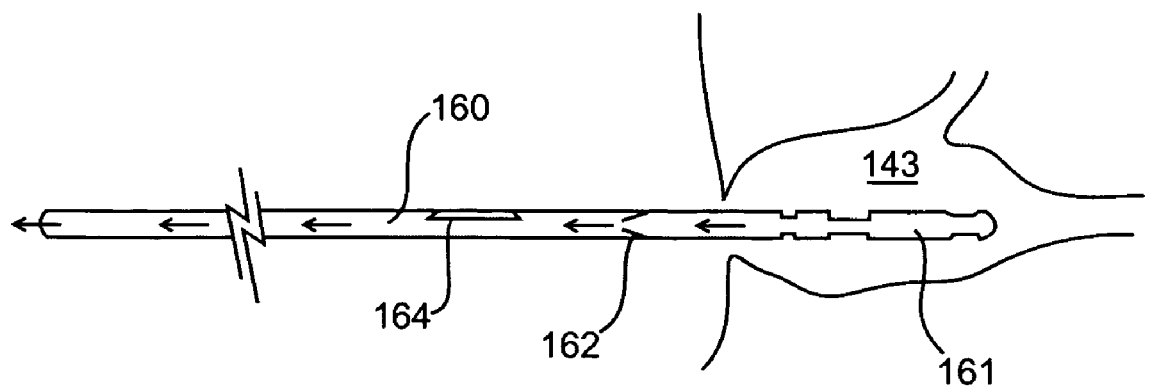
FIGS. 16A and 16B provide a depiction of a device that includes an active shunting element.
Figure 16B:
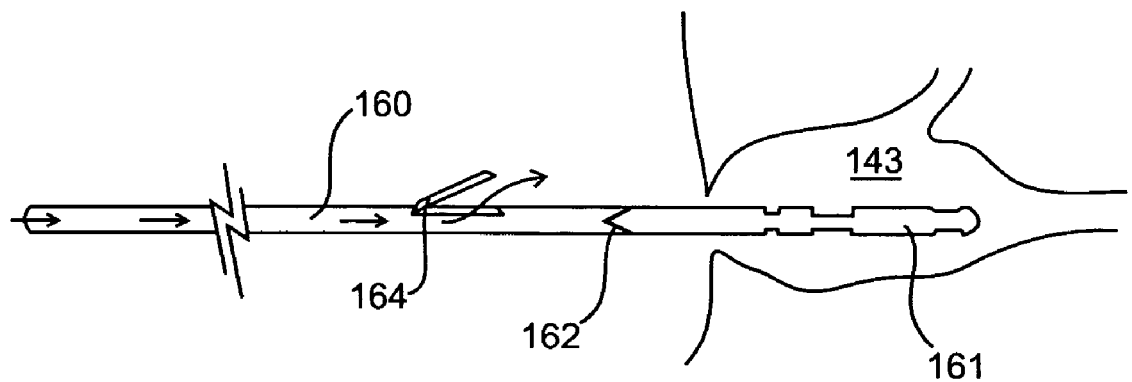

In certain embodiments, active shunting is employed, e.g., to achieve a desirable pressure profile in the target/efferent fluid collection site. An embodiment of a device that produces a reduced pressure at the collection site via active shunting is depicted in FIGS. 16A and 16B and includes an aspiration lumen 160, a distal portion 161 of the aspiration lumen through which all fluid from the collection site 143 tends to travel through, a one way valve mechanism 162 within that distal portion that generally only allows fluid to travel in the distal-to-proximal direction of the aspiration lumen and a re-entry port 164 proximal to the distal portion with a one way valve mechanism that generally only allows fluid to escape the aspiration lumen and re-enter the general circulation. When the proximal end of such an embodiment is connected to a cyclic pump that aspirates for a certain percentage of a cycle, and infuses for another percentage of the cycle, the net result is as follows: 1) during the aspiration portion, fluid is withdrawn from the collection site, and travels proximal along the length of the aspiration lumen (a sensor within the aspiration lumen can optionally detect the presence of the agent to be retrieved within the distal portion of the aspiration lumen at this time); and 2) during the infusion portion of the cycle, fluid proximal to the one-way valve is re-introduced to the general circulation as it travels in the proximal-to-distal direction back out the re-entry port. In these embodiments, when the agent is detected, the infusion portion of the cycle is skipped, allowing the removal of the fluid containing that agent. In certain embodiments, the one-way valve or selectively controllable re-entry port of these embodiments is implemented as described above for the case of the passive shunting embodiment (e.g., as depicted in FIGS. 15A and 15B). In certain embodiments, the one-way valve within the distal portion of the aspiration lumen is constructed using an intraluminal duckbill valve, or a piece of formed flexible plastic that operates in a manner similar to a bicuspid or tricuspid valve in the heart. In certain embodiments, a single cusp design is employed.

Figure 10:
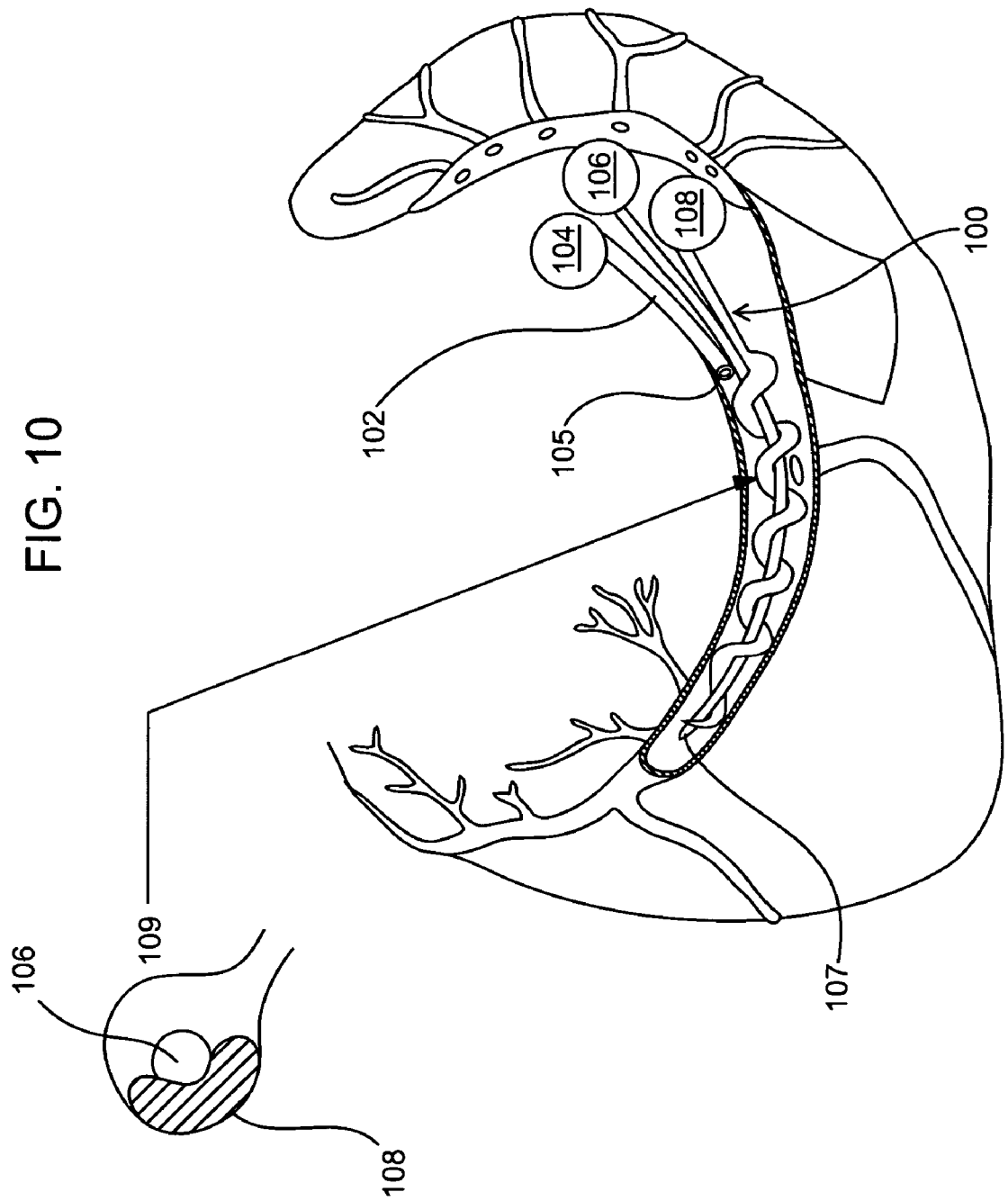
FIG. 10 provides a depiction of a device according to an embodiment of the present invention in which a spiral balloon element is present to modulate fluid flow through the coronary sinus.

FIG. 10 provides a depiction of an alternative device for collection of an agent from the coronary sinus using the methods of the subject invention, where the device includes a fluid-flow modulating element for modulating blood flow through the coronary sinus. In FIG. 10, device 100 includes three distinct elements at its general distal end 102, i.e., as aspiration lumen 104, a guidewire/sensor element 106 and a spiral balloon element 108. During use of the device as shown in FIG. 10, the distal end 107 of guidewire/sensor element 106 is positioned near the ostia of the cardiac veins so as to provide early detection of agent entering the coronary sinus. Spiral balloon element 108 spirals around the central guidewire/sensor element 106 an extends the length of the coronary sinus. The dimensions of the balloon are such that the fluid flow path of the coronary sinus is altered so that its length ranges from about 10 to about 300 mm, such as from about 15 to about 150 mm, and the diameter of the flow path as it spirals around the guidewire/sensor element 106 ranges from about 1 mm to about 50 mm, such as from about 1.5 mm to about 15 mm. The spiral balloon element 108 provides the ability to modulate the velocity of fluid flow through the coronary sinus, e.g., where the velocity of fluid flow may be controlled to range from about 10 ml/sec to about 500 ml/sec, such as from about 50 ml/sec to about 150 ml/sec. Several advantages are provided by the device depicted in FIG. 10. For example, by selecting the appropriate catheter to vessel lumen ratio, e.g., from about 1% to about 90%, such as from about 10% to about 70%, the flow of fluid through the coronary sinus can be controlled at a desirable rate. Furthermore, less negative pressure may need to be employed to ensure that fluid enters the aspiration element 104, whose distal end 105 is positioned at the proximal end of the spiral balloon element 108. Cross-sectional view 109 depicts the flow path in the coronary sinus and shows how the dimension are altered upon deployment of the device. Also, in certain embodiments such configuration provides advantages as an anchoring mechanism for the catheter tip to remain in the target vessel for the duration of the catheterization procedure.

In an alternative embodiment, a sprial balloon may be employed without the depicted central guidewire/sensor lumen depicted in FIG. 10. In these embodiments, the spiral balloon may serve to anchor the distal end of the device, but maintain a straight central fluid flow lumen, and therefore not lengthen the fluid flow may, which feature is desirable in certain embodiments.

As indicated, in each of the above embodiments, each aspiration lumen may optionally incorporate a detector, e.g., where the detector is integral to the aspiration element lumen, such as any of the representative detector embodiments that are described below.

Systems

Also provided are systems for use in practicing the subject methods, where the systems include a device for selectively removing agent from the efferent fluid collection site, such as the representative devices described above, and may optionally include one or more additional components that find use in practicing the subject methods, e.g., detectors, agent introducers, data recorders, etc. A representative system is depicted in FIG. 1. In the system depicted in FIG. 1, the system includes the standard device components, i.e., an aspiration controller 11 and aspiration mechanism 12 operatively linked to an aspiration lumen which is introduced into the subject (body) 13, as well as a number of additional/optional components, such as an injection/delivery system 14 for introducing agent into the body at a site upstream of the target efferent fluid collection site, one or more detector elements 15 for detecting the presence of agent in the efferent fluid collection site, and an aspiration recorder/display element 16 for recording data (e.g., fluid flow data, etc.) and displaying the same to the operator.

Utility

The subject invention finds use in a wide variety of different applications, including both diagnostic and therapeutic applications. Of particular interest is the use of the subject methods and devices to selectively remove from a subject a locally administered diagnostic or therapeutic agent, so that the host or subject is not systemically exposed to the diagnostic or therapeutic agent.

In many embodiments, the subject methods are employed to selectively remove a locally administered diagnostic agent, such that the diagnostic agent is only contacted with a limited region or portion of the host to which it is administered, e.g., a specific organ or portion thereof. A common example of such a compound is radio-opaque dye. Iodinated forms of such a dye are used routinely during catheter-based interventional procedures such as coronary, renal, neurological and peripheral arteriography. The iodine component has a high absorption of x-rays and therefore provides a contrast medium for the radiological identification of vessels when introduced within an upstream artery. However, the use of such dyes is known to have potential toxic effects depending on the specific formulation, including direct injury to renal tubule cells, endothelial injury, bronchospasm, inflammatory reactions, pro-coagulation, anti-coagulation, vasodilation and thyrotoxicosis.

Another representative utility of the subject invention is in the selective removal from a patient of a locally administered therapeutic agent, where representative therapeutic agents or materials that may be introduced locally for desired effects but whose direct or other effects would be undesired elsewhere include vasoactive agents, cytotoxic agents, genetic vectors, apoptotic agents, anoxic agents (including saline), photodynamic agents, emboli-promoting particles or coils, antibodies, cytokines, immunologically targeted agents and hormones. Additional agents of interest include, but are not limited to: cells, enzymes, activators, inhibitors and their precursors, as well as sclerosing agents, anti-inflammatories, pro-inflammatories, steroids and osmotic agents, and the like. As such, another representative application of the subject methods is to determine the amount of agent retained at a local area or region of a subject upon local administration of the agent to the subject. For example, where a therapeutic agent is locally administered to a region or location of a subject, e.g., an organ, and blood carrying the agent is selectively removed from the subject according to the subject methods, the amount of agent in the collected blood can be used to determine the amount of agent that was retained by the local region or area, e.g., organ, of the subject. As such, in those cases where the present invention is used to retrieve a diagnostic or therapeutic agent for which a portion of that agent desirably resides in the region into which it is delivered, and the portion of the agent collected from the collection represents an amount of the agent that did not remain resident in that region, the subject methods may be employed to estimate the effective dosage of the agent. For example, in the localized delivery of a chemotherapeutic agent via the afferent branches of a targeted tumor, the present invention is capable of collecting some of the chemotherapeutic agent before it is able to enter into the systemic circulation, thus minimizing its side effects. The difference between the amount of agent injected and the amount of agent that is retrieved by the present invention represents the sum of the amount of agent that was successfully incorporated into the tumor and the amount of agent that escaped to the systemic circulation. If a goal of the localized delivery of the chemotherapeutic agent is to attempt to incorporate a given dosage of the agent into the tumor, it is possible to use the present invention to better estimate how much of the delivered agent was successfully incorporated into the tumor by estimating how much of the agent was retrieved in the collection site. If a higher than expected amount of agent was retrieved in the collection site, than a substantial portion of the agent was not successfully incorporated into the tumor and this may direct the physician to deliver more agent to the tumor, or consider alternative strategies for treatment. The higher the efficacy of the present invention is in terms of retrieving the agent, the more accurate the estimate of the amount of agent successfully delivered to the site will become.

Kits

Also provided are kits for use in practicing the subject methods, where the kits typically include one or more of the above devices, and/or components of the subject systems, as described above. As such, a representative kit may include a device, such as a catheter device, that includes an aspiration lumen, aspiration mechanism and aspiration mechanism controller, as described above. The kit may further include other components, e.g., guidewires, etc., which may find use in practicing the subject methods.

In addition to above mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following example is offered by way of illustration, and not by way of limitation.

EXPERIMENTAL

I. Contrast Retrieval from the Coronary Sinus During Coronary Angiography

An Experimental Study

A. Methods:

A 10F guiding catheter was placed in the coronary sinus of a porcine animal model just distal to the azygous vein.

The external diameter of the guiding catheter was sub-occlusive for the target segment of the porcine coronary sinus, such that the sheath permitted flow to observably varying degrees. A coronary guiding catheter was placed at the ostium of the left coronary arterial system.

Aspiration was enabled using a "bleed-back mechanism" wherein a valve along the proximal portion of the aspiration lumen was controlled by a human operator. The proximal end of the aspiration lumen emptied into a small container with graduated volume markings. The mechanical driving forces for aspiration was provided via a combination of gravity and the pressure difference between the venous system and the ambient environment. The volume of the lumen of the aspiration lumen was measured to be 4 cubic centimetres.

10 cubic centimeters of contrast agent were injected into the left coronary arterial system. These injections were given slowly to minimize regurgitation of contrast into the aorta, which would result in contrast being injected that could not be retrieved from the coronary sinus. The migration of contrast agent towards the coronary sinus was observed fluoroscopically by the human operator. As the contrast was visualized to enter the anterior interventricular vein, just upstream of the coronary sinus, the human operator opened the valve of the aspiration lumen. The first 4 cc of fluid was collected in one container, corresponding to fluid that was resident in the aspiration lumen prior to opening the valve. The following 10 cc of fluid was then collected in a second container.

The hematocrit of the second container was then measured using standard laboratory techniques and compared with the hematocrit of the systemic circulation of the animal which was measured 5 minutes after the injection of contrast agent.

The process of injecting contrast agent, followed by aspiration from the coronary sinus into 2 containers and comparison of the hematocrit of the second container with that of the systemic circulation was repeated 5 times.

B. Results:

The efficiency of removal of contrast was estimated as follows:

The hematocrit of the aspirated fluid can be represented as:

$$Hct = \frac{RBC\_volume}{plasma\_vol + RBC\_vol + contrast\_vol} \quad (1)$$

where the denominator is known to be 10 cc, making it easy to calculate RBC_volume by the following:

$$RBC\_volume = Hct * 10 \text{ cc}$$

Furthermore, the plasma volume can be expressed as RBC volume multiplied by a factor calculated from the baseline hematocrit:

$$Baseline = \frac{RBC\_volume}{RBC\_volume + plasma\_volume}$$

which can be rearranged to:

$$plasma\_volume = \frac{RBC\_volume \times (1 - baseline)}{baseline}$$

(1) can further be rearranged to express contrast_volume as a function of hematocrit as follows:

$$contrast\_vol = \frac{RBC\_vol}{Hct} - (plasma\_vol + RBC\_vol)$$

Using this latter equation, the volume of contrast agent retrieved can be estimated, which can directly be expressed as a percentage of the original 10 cc of contrast injected. For the 5 iterations of this illustrative experiment, the percentages of original contrast injected that was successfully retrieved were calculated to be 62.5%, 51.5%, 33.8%, 58.4%, 37.3%.

It should be noted that this experiment was performed for proof of concept purposes only and the demonstrated efficiencies of contrast retrieval likely understate the results achievable. The incorporation of automated detection, as well as optimization of injection and aspiration parameters (e.g. volumes, rates) will most certainly improve these results. Furthermore, improved results within humans are more likely, given that the coronary sinus in porcine models also receives flow from the azygous vein, which is not the case in humans.

II. Representative Protocols for Selective Removal of Contrast Agent from the Coronary Sinus A. First Representative Protocol 1. The patient is prepared for conventional cardiac catheterization procedure, including field sterilization, draping and any necessary medications.
2. The physician uses catheterization techniques, such as the Seldinger technique, and catheterization tools, such as guidewires and guiding catheters, to access a left-sided coronary artery via an entry point at the femoral artery near the groin
3. The physician uses catheterization techniques, such as the Seldinger technique, and catheterization tools, such as guidewires and guiding catheters, to access the coronary sinus via an entry point at the femoral vein near the groin.
4. A catheter for inserting contrast agent into the coronary artery is advanced to the site at which contrast is to be introduced.
5. An aspiration lumen is advanced to the coronary sinus, along with a fiber optic that is incorporated in the aspiration lumen.
6. The aspiration controller is turned on so that the fiber optic can be used to detect a decrease in the concentration of blood in the coronary sinus (and hence an increase in concentration of contrast agent).
7. A bolus of contrast agent is injected at the site to which contrast is to be introduced.
8. As the bolus of contrast agent migrates through the arterial system, followed by the myocardial capillaries and eventually enters the coronary sinus, it is detected by the fiber optic detector within the coronary sinus.
9. The aspiration controller responds to the entry of contrast agent into the coronary sinus by activating an aspiration mechanism at the proximal end of the aspiration lumen.

10. As the concentration of contrast agent decreases in the coronary sinus, the detector approaches a threshold at which it signals the controller to cease aspiration.
11. Steps 7 through 10 can be repeated several times to remove contrast during subsequent cycles of contrast injection.
12. Upon completion of use, the aspiration lumen is withdrawn from the body. The aspirated fluid will contain a significant portion of the contrast agent introduced during the procedure.

B. Second Representative Protocol

The protocol is performed substantially as described in II.A. above, with the exception that presence of the agent in the coronary sinus is detected by cycling small samples of fluid from the distal tip of the device and then returning the fluid back out into the circulation if.

C. Third Representative Protocol

The protocol is performed substantially as described in II.A. above, with the additional step of temporarily stenting the small cardiac vein to get better collection from the right side of the heart.

D. Fourth Representative Protocol

The protocol is performed substantially as described in II.A. above, with the additional step of covering the AV ridge to prevent contrast from leaking back into the right atrium from the small cardiac vein (SCV), thus redirecting that fluid to travel through the SCV into the CS.

III. Catheter Based Detection of Radiocontrast Media

A. Introduction

Several conditions in the cornary artery injection of radiocontrast media, such as injection volume (10 cc), time of injection (1–2 sec), and the high viscosity of the radiocontrast media, account for limited mixing of the radiocontrast media with the blood in the coronary artery. The radiocontrast media consequently tends to flow through the vasculature as a bolus. The red blood content in the radiocontrast bolus is reduced compared to the blood prior to the radiocontrast injection. Hematocrit measurement therefore is an indirect method of detecting radiocontrast media in blood. One means of hematocrit measurement is sensing the reflectance properties of red blood cells. A pair of send and receive optical fibers incorporated in the catheter distal tip to detect red blood cell backscattered light are employed in the following experiment. Prior to radiocontrast injection, the blood is expected to produce the largest reflected light and the signal is expected to diminish due to a drop in red blood content as the concentration of radiocontrast media increases.

B. Sensor

Figure 17:
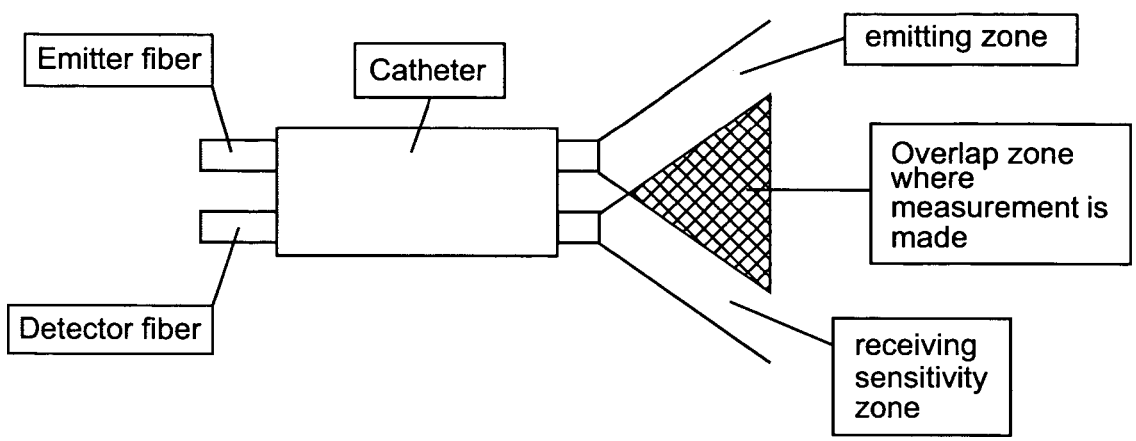
FIG. 17 provides a representation of a device employed in the Experimental Section, below.

FIG. 17 is a cross sectional view of the distal tip of an 8 Fr catheter with a pair of 500 μm emitter and detector glass fibers. The light emitter is a near infrared LED of 950 nm wavelength, because it is a very efficient emitter, and because photodetectors are intrinsically well matched to this wavelength. The 950 nm light is emitted axially from the distal tip of the catheter and the fibers are positioned so that there is no overlap in the emitting zone and receiving zones enabling reflectance measurements as the blood flowed past the distal tip of the catheter.

During use, the electronic circuit delivers a pulse of approximately 500 ma for 100 microseconds with a repetition rate of 120 Hz into the emitter LED. The signal from the photodetector is conditioned and sampled synchronously with the drive signal, after the initial transient is complete, approximately halfway through the pulse. This signal is then low pass filtered and the output monitored on an oscilloscope.

C. In Vitro Experimental Results

Figure 18:
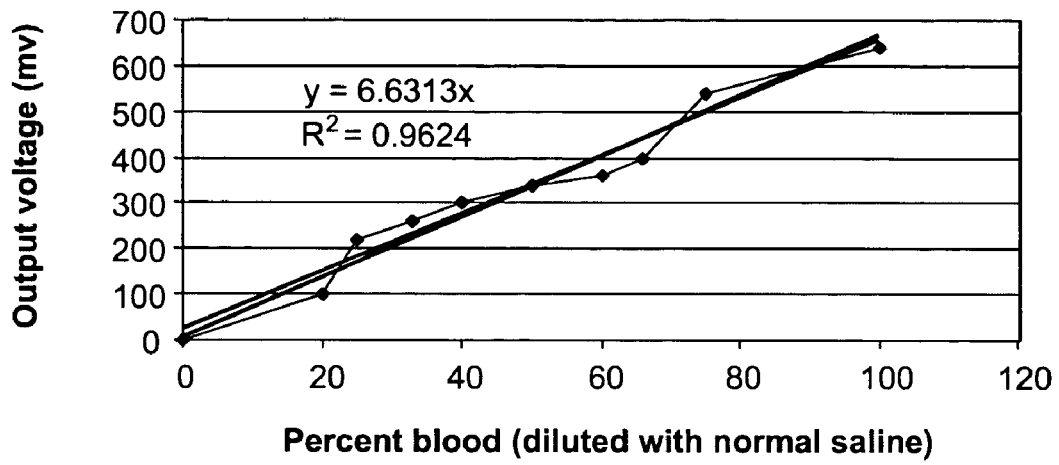

Citrated pig blood with a hematocrit of approximately 35% was pipetted using in 1 ml increments, and added to a container with the appropriate amount of normal saline to make the required dilutions. Saline was used as diluant to mimic the effects on red blood cell volume when radiocontrast media is administered in the course of coronary angiography. Measurements were made from 0% blood to 100% blood by inserting the tip of the catheter in the blood samples and monitoring the output voltage. The results obtained from this proof of concept experiment are shown in FIG. 18.

Figure 19:
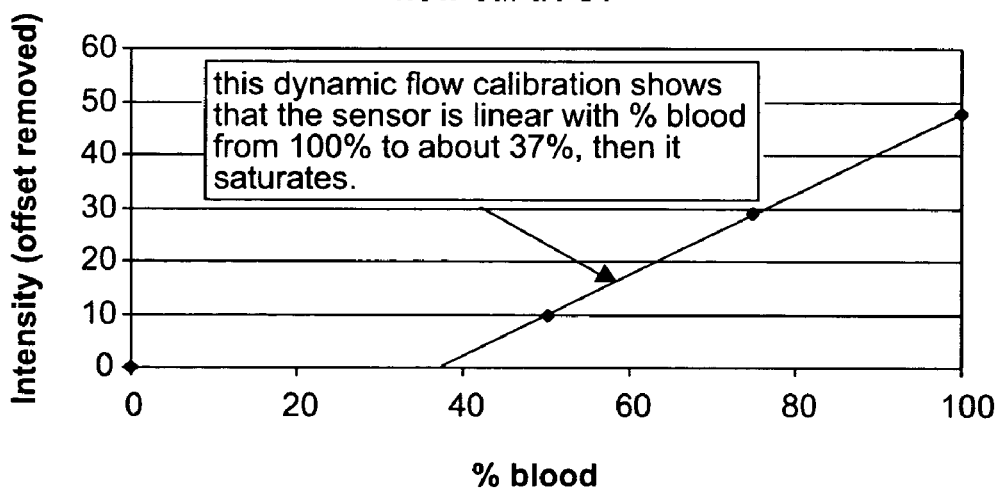

D. In Vivo Experimental Results:

Calibration was performed on the bench in advance of the animal experiment, using citrated pig blood and the Isovue 370 radiographic contrast medium. Static calibrations were non-linear, perhaps due to settling of blood cells or formation of rolleau. Dynamic experiments with flowing blood with injection of blood diluted with contrast demonstrated a linear relationship between % blood and intensity of backscattered light. The response was linear for blood in the range of 100% to about 40% blood as shown below in FIG. 19. Since the starting blood sample had a hematocrit of about 35%, the linear response range corresponded to a change in hematocrit from 35% to roughly 14%.

A pig, approximately 4 months and 30 kilograms, was initially immobilized with an intramuscular injection of ketamine (20 mg/kg) and xylazine (2 mg/kg). Following intubation, the animal was mechanical ventilated with a mixture of air and 0.5% halothane to maintain anesthesia during the course of the procedure. A surgical cut down procedure was performed on the right femoral artery and a sheath was inserted to create vascular access. A guide catheter was then inserted through the sheath and advanced under angiographic guidance into the ostium of the left coronary artery. A second surgical cut down procedure was then performed on the right carotid artery followed by insertion of a sheath. A guide catheter was then inserted and advanced under angiographic guidance through the right atrium and into the coronary sinus. The catheter shown in FIG. 17 was then inserted through the guide catheter and advanced so that the distal tip including the sensing element extended into the coronary sinus in contact with the venous blood flow. The venous blood flow in the coronary sinus was not occluded by the catheter.

Once positioned in the coronary sinus the detector is activated and the electronic signal induced by the red blood reflectance was monitored on an oscilloscope until a stable baseline signal was achieved. Radiocontrast media (Isovue-370, Bracco Diagnostics, iopamidol at 755 mg/ml) was power injected over a 1–2 second interval into the left coronary artery. At the point of radiocontrast injection, two means of detecting the radiocontrast were monitored: (a) the change in red blood induced reflectance by the catheter; and (b) the time of appearance and subsequent disappearance of the fluoroscopic image of the venous return of radio-opaque material in the coronary sinus. Five sequences of radiocontrast injection in the left coronary artery followed by detection were performed.

At the end of the procedure the catheters were removed and the animal was euthanized with an intravenous injection of pentobarbital.

When a power injector was used to inject contrast into the left coronary artery of the pig, the signals observed in five runs are shown in FIG. 20. The raw signal was displayed as percentage radiocontrast using the calibration curve above. The injections were in five consecutive trials: three runs each consisting of 10 cc of radiocontrast media delivered uniformly within 2 seconds, one run of 5 cc delivered within 1 second, and one run of 1 cc delivered within 1 second. The lower margin of the chart in FIG. 20 shows fluoroscopic signal markers. The beginning edge of the markers show the time when the injection began and the time when the radiocontrast became subjectively visible on the fluoroscope. Total time for data collection for each radiocontrast injection run was 15 seconds.

Results for the 5 and 10 cc injections show a correlation between the time the catheter senses a change in reflectance in the coronary sinus and the appearance of the radiocontrast in the coronary sinus as visualized on the fluoroscope. The data shows that the sensor measuring radiocontrast induced changes in blood reflectance is a feasible means of activating catheter based aspiration of radiocontrast/blood mixtures in the coronary sinus. The 1 cc injection, although visible on the fluoroscopy, was not detected with the sensor and represents the sensitivity limit with the current embodiment of the optical device. Since most angiographic procedures utilize 5 or 10 cc contrast injections, failure to detect 1 cc injections does not represent a practical limitation of the device. Sensitivity can be most readily improved by reducing electronic noise in the baseline reflectance signal before contrast injection. It was observed that the greatest source of the electronic noise was due to the tip of the catheter moving around in the coronary sinus as the heart was beating and contacting the wall of the vessel. Means of isolating the sensor to prevent wall contact would be the most straightforward means to reduce the electronic noise thus improve sensitivity.

It is evident from the above discussion and results that the subject invention provides a significantly improved method of locally administering an agent, e.g., a diagnostic or therapeutic agent, to a host. Advantages of using the subject invention to remove an agent from a fluid collection site include: (a) a reduction in systemic side effects; and (b) the ability to increase concentration and/or amount of substance that can be used safely to achieve desired diagnostic/therapeutic result. Advantages of the subject non-occlusive methods over occlusive methods include: (a) minimal structural changes occur while performing the methods so that complications arising from structural changes (e.g. morphological changes to coronary sinus may predispose to arrhythmias and expansion of cerebral veins may induce migraine) are avoided; (b) the limitation of modulation of flow through the upstream organ because of minimized changes (e.g. less elevation) of venous-side pressure is achieved; (c) potentially greater efficiency with respect to the amount of non-targeted (innocent bystander) fluid that is removed; (d) less traumatic impact to the subject than some rapidly expandable implementations of occlusive members; and (e) more fault-tolerant, as default state is to allow flow to continue as usual when there is no signal to cause removal of substances. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for removing contrast agent from a physiological efferent fluid collection site of a body, said method comprising:
    introducing a non-occlusive aspiration element to a target site at least proximal to said physiological efferent fluid collection site; and
    activating said aspiration element when said contrast agent is at least predicted to be present in said target site to selectively remove fluid comprising said contrast agent from said physiological efferent fluid collection site;
    wherein said aspiration element does not occlude said target site when activated and said removed fluid is not returned to the body.

2. The method according to claim 1, wherein said physiological efferent fluid collection site is a vascular fluid collection site.

3. The method according to claim 2, wherein said vascular fluid collection site is a cardiovascular fluid collection site.

4. The method according to claim 3, wherein said cardiovascular fluid collection site is a coronary cardiovascular fluid collection site.

5. The method according to claim 4, wherein said coronary cardiovascular fluid collection site is a coronary sinus.

6. The method according to claim 1, wherein said physiological efferent fluid collection site is present in a mammal.

7. The method according to claim 6, wherein said mammal is a human.

8. The method according to claim 1, wherein said non-occlusive aspiration element comprises a detector for at least predicting the presence of said agent in said physiological efferent fluid collection site, wherein said detector is located at an upstream location of said non-occlusive aspiration element.

9. The method according to claim 8, wherein said detector is located at the vicinity of said target site.

10. The method according to claim 8, wherein said detector is a fiber-optic detector.

11. A method for removing an agent from a physiological efferent fluid collection site of a body, said method comprising:
    introducing a non-occlusive aspiration element to a target site at least proximal to said physiological efferent fluid collection site, wherein said non-occlusive aspiration element comprises a detector for at least predicting the presence of said agent in said physiological efferent fluid collection site and said detector is located at an upstream location of said non-occlusive aspiration element; and
    activating said aspiration element when said agent is at least predicted to be present in said target site to selectively remove fluid comprising said agent from said physiological efferent fluid collection site;

wherein said aspiration element does not occlude said target site when activated and said removed fluid is not returned to the body.

12. The method according to claim 11, wherein said physiological efferent fluid collection site is a vascular fluid collection site.

13. The method according to claim 12, wherein said vascular fluid collection site is a cardiovascular fluid collection site.

14. The method according to claim 13, wherein said cardiovascular fluid collection site is a coronary cardiovascular fluid collection site.

15. The method according to claim 14, wherein said coronary cardiovascular fluid collection site is a coronary sinus.

16. The method according to claim 11, wherein said physiological efferent fluid collection site is present in a mammal.

17. The method according to claim 16, wherein said mammal is a human.

18. The method according to claim 11, wherein said agent is a therapeutic agent.

19. The method according to claim 11, wherein said agent is a diagnostic agent.

20. The method according to claim 19, wherein said diagnostic agent is a contrast agent.

21. The method according to claim 11, wherein said detector is a fiber-optic detector.

22. The method according to claim 11, wherein said detector is located at the vicinity of said target site.

* * * * *